United States Patent
Ibata

(10) Patent No.: US 12,221,556 B2
(45) Date of Patent: Feb. 11, 2025

(54) HARD-MASK FORMING COMPOSITION, METHOD FOR MANUFACTURING ELECTRONIC COMPONENT, AND COMPOUND AND RESIN

(71) Applicant: TOKYO OHKA KOGYO CO., LTD., Kawasaki (JP)

(72) Inventor: Keiichi Ibata, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 995 days.

(21) Appl. No.: 16/950,614

(22) Filed: Nov. 17, 2020

(65) Prior Publication Data
US 2021/0155825 A1    May 27, 2021

(30) Foreign Application Priority Data
Nov. 22, 2019   (JP) .................................. 2019-211731

(51) Int. Cl.
| | |
|---|---|
| C09D 179/04 | (2006.01) |
| C07C 225/22 | (2006.01) |
| C07D 209/86 | (2006.01) |
| C07D 209/90 | (2006.01) |
| C08G 73/02 | (2006.01) |
| C08G 73/06 | (2006.01) |
| C09D 179/02 | (2006.01) |
| G03F 7/09 | (2006.01) |
| H01L 21/027 | (2006.01) |

(52) U.S. Cl.
CPC .......... *C09D 179/04* (2013.01); *C07C 225/22* (2013.01); *C07D 209/86* (2013.01); *C07D 209/90* (2013.01); *C08G 73/026* (2013.01); *C08G 73/0672* (2013.01); *C09D 179/02* (2013.01); *G03F 7/092* (2013.01); *H01L 21/0274* (2013.01)

(58) Field of Classification Search
CPC .. C09D 179/04; C09D 179/02; C07D 209/86; C07D 209/82; C07D 209/90; C07C 225/22; C08G 73/0672; G03F 7/11
See application file for complete search history.

(56) References Cited

U.S. PATENT DOCUMENTS

| | | | | |
|---|---|---|---|---|
| 2012/0181251 | A1* | 7/2012 | Minegishi | G03F 7/11 216/49 |
| 2017/0008843 | A1 | 1/2017 | Kwon et al. | |
| 2019/0064659 | A1 | 2/2019 | Kori et al. | |
| 2019/0354018 | A1* | 11/2019 | Tokunaga | C08G 73/1078 |
| 2020/0348595 | A1* | 11/2020 | Ehara | G03F 7/094 |
| 2021/0116814 | A1 | 4/2021 | Tokunaga et al. | |

FOREIGN PATENT DOCUMENTS

| | | | | |
|---|---|---|---|---|
| CN | 109212902 | A | | 1/2019 |
| JP | S60-070437 | A | | 4/1985 |
| JP | 61-239243 | A | | 10/1986 |
| JP | 62-025744 | A | | 2/1987 |
| JP | 2001-051422 | A | | 2/2001 |
| JP | 2009-149764 | A | | 7/2009 |
| JP | 2010140976 | A | * | 6/2010 |
| JP | 2014-010408 | A | | 1/2014 |
| JP | 2015-091775 | A | | 5/2015 |
| JP | 2017-014191 | A | | 1/2017 |
| JP | 2019-044022 | A | | 3/2019 |
| KR | 20190002987 | A | * | 1/2019 ............. G03F 7/004 |
| WO | WO 2011/040340 | A1 | | 4/2011 |
| WO | WO-2019146378 | A1 | * | 8/2019 ........... C07C 233/65 |
| WO | WO 2019/225615 | A1 | | 11/2019 |

OTHER PUBLICATIONS

English Machine Translation of KR20190002987A (Year: 2019).*

* cited by examiner

*Primary Examiner* — Mark F. Huff
*Assistant Examiner* — Nicholas E Brown
(74) *Attorney, Agent, or Firm* — Knobbe, Martens, Olson & Bear, LLP

(57) ABSTRACT

A hard-mask forming composition that forms a hard mask that is used in lithography, the hard-mask forming composition including at least one of a compound represented by General Formula (sc-1) and a resin having a partial structure represented by General Formula (sc-p1). In the general formula, $R^{11}$ and $R^{12}$ are organic groups having 1 to 40 carbon atoms or hydrogen atoms; $R^{13}$ and $R^{14}$ are aromatic hydrocarbon groups having 6 to 30 carbon atoms which may have a substituent; $R^{13}$ and $R^{14}$ may be bonded to each other to form a structure having an aromatic heterocyclic ring, and the hydrogen atom of the phenylene group in the formula may be substituted with a substituent

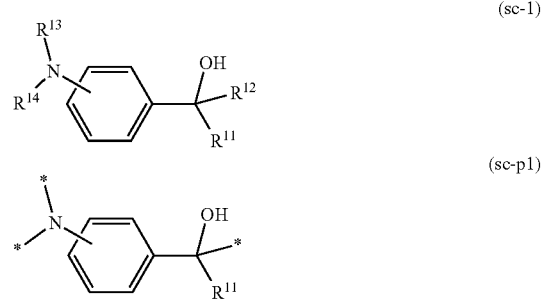

13 Claims, 4 Drawing Sheets

HARD-MASK FORMING COMPOSITION, METHOD FOR MANUFACTURING ELECTRONIC COMPONENT, AND COMPOUND AND RESIN

BACKGROUND OF THE INVENTION

Field of the Invention

The present invention relates to a hard-mask forming composition, a method for manufacturing an electronic component, and a compound and a resin.

Priority is claimed on Japanese Patent Application No. 2019-211731, filed on Nov. 22, 2019, the content of which is incorporated herein by reference.

Description of Related Art

Generally, in semiconductor manufacturing, a laminate in which a resist film is formed on a substrate, such as a silicon wafer, is subjected to processing including dry etching, for example, a treatment in which a resist film is selectively exposed to form a resist pattern on the resist film, and dry etching is performed using thereof as a mask, thereby forming a pattern on the substrate.

As a pattern forming method using a resist film, a three-layer resist method is known (for example, see Japanese Unexamined Patent Application First Publication No. 2001-51422). The three-layer resist method is that, first, an organic hard mask layer is formed using an organic material on a support, an inorganic hard mask layer is formed thereon using an inorganic material, and then a resist film is further formed on the inorganic hard mask layer. Subsequently, a resist pattern is formed by typical lithography, an inorganic hard mask pattern is formed by etching the inorganic hard mask layer with the resist pattern as a mask, and then an organic hard mask pattern is formed by etching the organic hard mask layer with the inorganic hard mask layer pattern as a mask. Then, the support is processed by being etched with the organic hard mask pattern as a mask.

Additionally, a two-layer resist method with fewer steps than the three-layer resist method has also been proposed (for example, see Japanese Unexamined Patent Application First Publication No. S61-239243 and Japanese Unexamined Patent Application First Publication No. S62-025744). The two-layer resist method is that the organic hard mask layer is provided on the support in the same manner as in the three-layer resist method, and then the resist film is provided on the organic hard mask layer. Subsequently, the resist pattern is formed by typical lithography, and the organic hard mask pattern is formed by etching the organic hard mask layer with the resist pattern as a mask. Then, the support is processed by being etched with the organic hard mask pattern as a mask.

As a method of forming the organic hard mask layer, a chemical vapor deposition method (hereinafter, sometimes referred to as a CVD method) is known in the related art. The CVD method uses amorphous carbon as a hard-mask forming material and has problems including slow throughput and expensive equipment investment.

Therefore, in recent years, a film forming technique by a spin-on-coating (SOC) method has been introduced (see, for example, Japanese Unexamined Patent Application First Publication No. 2015-91775). An organic hard-mask forming material applicable to the SOC method has been proposed. The SOC method has advantageous effects of high throughput and usability of an existing spin coater as compared with the CVD method.

The hard-mask forming material is required to have high etching resistance and solvent resistance in order to function as a mask for substrate processing. In addition, since the hard-mask forming material is required to withstand a high temperature at the time of forming the inorganic hard mask layer, heat resistance is also required.

Generally, as the organic hard-mask forming material, a composition containing a specific resin containing an aromatic ring, from a viewpoint of etching resistance, and a crosslinking agent, from a viewpoint of solvent resistance and heat resistance, is used.

CITATION LIST

Patent Literature

[Patent Literature 1] Japanese Unexamined Patent Application First Publication No. 2001-51422
[Patent Literature 2] Japanese Unexamined Patent Application First Publication No. S61-239243
[Patent Literature 3] Japanese Unexamined Patent Application First Publication No. S62-025744
[Patent Literature 4] Japanese Unexamined Patent Application Publication No. 2015-91775

SUMMARY OF THE INVENTION

However, a hard-mask forming material containing a crosslinking agent having a small molecular weight in the related art has a problem that outgassing is easily generated at a time of baking when processing a support.

In addition, in recent years, as a high aspect ratio of etching processing has been proceeded, the hard-mask forming material is required to have higher etching resistance than before.

The present invention is made in view of the problems stated above, and an object of the present invention is to provide a hard-mask forming composition having higher etching resistance and excellent in solvent resistance and heat resistance, a method for manufacturing an electronic component using the hard-mask forming composition, and a material useful for the hard-mask forming composition.

The present invention adopted the following composition in order to solve the problems.

That is, a first aspect of the present invention is a hard-mask forming composition, which forms a hard mask that is used in lithography, including at least one selected from the group consisting of a compound (SC) represented by General Formula (sc-1) and a resin (P) having a partial structure represented by General Formula (sc-p1).

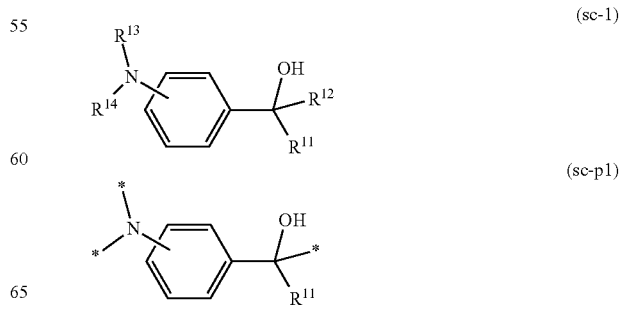

[In the formula, $R^{11}$ and $R^{12}$ each independently are an organic group having 1 to 40 carbon atoms or a hydrogen atom. $R^{13}$ and $R^{14}$ each independently are an aromatic hydrocarbon group having 6 to 30 carbon atoms, which may have a substituent. Here, $R^{13}$ and $R^{14}$ may be bonded to each other to form a structure having an aromatic heterocyclic ring. In addition, a hydrogen atom of a phenylene group in the formula may be substituted with a substituent. * indicates a bond].

A second aspect of the present invention is a method for manufacturing an electronic component including: forming a hard mask layer (m1) on a support using the hard-mask forming composition according to the first aspect; and processing the support using the hard mask layer (m1) as a mask.

A third aspect of the present invention provides a method for manufacturing an electronic component, including: forming a hard mask layer (m1) on a support using the hard-mask forming composition according to the first aspect; forming a hard mask layer (m2) made of an inorganic material on the hard mask layer (m1); forming a resist film on the hard mask layer (m2); forming a resist pattern on the hard mask layer (m2) by exposing the resist film to light and developing the exposed resist film; forming an inorganic pattern by etching the hard mask layer (m2) using the resist pattern as a mask; forming a film-forming component pattern by etching the hard mask layer (m1) using the inorganic pattern as a mask; and processing the support using the film-forming component pattern as a mask.

A fourth aspect of the present invention provides a method for manufacturing an electronic component, including: forming a hard mask layer (m1) on a support using the hard-mask forming composition according to the first aspect; forming an inorganic pattern made of an inorganic material on the hard mask layer (m1); forming a film-forming component pattern by etching the hard mask layer (m1) using the inorganic pattern as a mask; and processing the support using the film-forming component pattern as a mask.

A fifth aspect of the present invention is a compound represented by General Formula (sc-1).

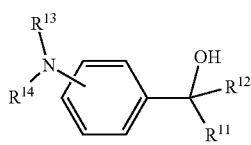

(sc-1)

[In the formula, $R^{11}$ and $R^{12}$ each independently are an organic group having 1 to 40 carbon atoms or a hydrogen atom. $R^{13}$ and $R^{14}$ each independently are an aromatic hydrocarbon group having 6 to 30 carbon atoms, which may have a substituent. Here, $R^{13}$ and $R^{14}$ may be bonded to each other to form a structure having an aromatic heterocyclic ring. In addition, a hydrogen atom of a phenylene group in the formula may be substituted with a substituent.]

A sixth aspect of the present invention is a resin having a partial structure represented by General Formula (sc-p1).

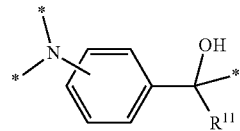

(sc-p1)

[In the formula, $R^{11}$ is an organic group having 1 to 40 carbon atoms or a hydrogen atom. The hydrogen atom of the phenylene group in the formula may be substituted with a substituent. * indicates a bond.]

A seventh aspect of the present invention is a compound represented by General Formula (sc-01-1).

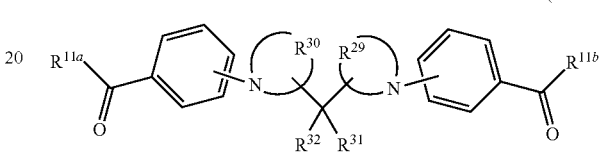

(sc-01-1)

[In the formula, $R^{11a}$ and $R^{11b}$ each independently are an organic group having 1 to 40 carbon atoms or a hydrogen atom. $R^{29}$ is a group that forms an aromatic heterocyclic ring together with a nitrogen atom. $R^{30}$ is a group that forms an aromatic heterocyclic ring together with a nitrogen atom. $R^{31}$ and $R^{32}$ each independently are an aromatic hydrocarbon group having 6 to 30 carbon atoms, which may have a substituent, or a hydrogen atom. Here, $R^{31}$ and $R^{32}$ may be bonded to each other to form a structure having an aromatic ring. In addition, the hydrogen atom of the two phenylene groups in the formula may be substituted with a substituent].

An eighth aspect of the present invention is a resin having a partial structure represented by General Formula (sc-p01).

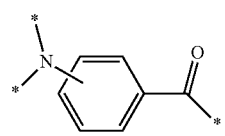

(sc-p01)

[In the formula, * indicates a bond].

According to the present invention, it is possible to provide a hard-mask forming composition having higher etching resistance, and excellent in solvent resistance and heat resistance, a method for manufacturing an electronic component using the same, and a material useful for the hard-mask forming composition.

DETAILED DESCRIPTION OF THE INVENTION

Figure 1:
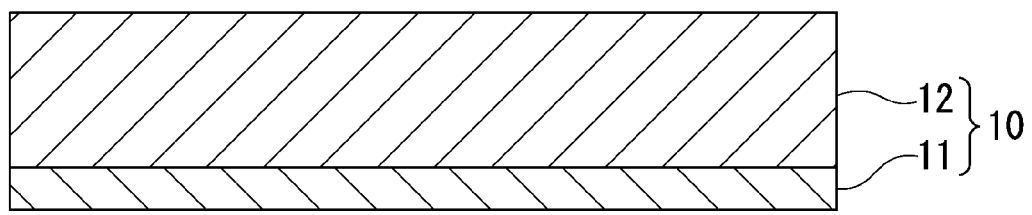
FIG. 1 is a cross-sectional view showing an exemplified support used in a method for manufacturing an electronic component according to an embodiment of the present invention.

In the specification and claims of the present invention, the term "aliphatic" is a relative concept to aromatic, and is defined to mean a group, a compound, or the like, which has no aromaticity.

The term "alkyl group" is intended to encompass linear, branched and cyclic monovalent saturated hydrocarbon groups, unless otherwise specified. The same definition applies to an alkyl group in an alkoxy group.

The term "alkylene group" is intended to encompass linear, branched, and cyclic divalent saturated hydrocarbon groups, unless otherwise specified.

The term "halogenated alkyl group" refers to a group in which a part or all of the hydrogen atoms of the alkyl group are substituted with halogen atoms, and examples of the halogen atom include a fluorine atom, a chlorine atom, a bromine atom, and an iodine atom.

The term "fluorinated alkyl group" or "fluorinated alkylene group" refers to a group in which a part or all of hydrogen atoms of an alkyl group or an alkylene group are substituted with fluorine atoms.

The term "structural unit" refers to a monomer unit constituting a polymer compound (resin, polymer, or copolymer).

The expression "may have a substituent" includes both cases where a hydrogen atom (—H) is substituted with a monovalent group, and where a methylene group (—CH$_2$—) is substituted with a divalent group.

The term "exposure" is a concept that includes general radiation irradiations.

In the specification and claims of the present invention, some structures represented by a chemical formula have an asymmetric carbon, and there may be enantiomers and diastereomers. Those isomers are collectively represented by one formula. The isomers may be used alone, or may be used as a mixture.

(Hard-Mask Forming Composition)

The hard-mask forming composition according to the first aspect of the present invention is a composition for forming a hard mask that is used in lithography.

The hard-mask forming composition of the present embodiment contains a film-forming component which is a base component of the hard mask layer. This film-forming component includes at least one selected from the group consisting of the compound (SC) represented by General Formula (sc-1) to be stated later and the resin (P) having a partial structure represented by General Formula (sc-p1). The compound (SC) and the resin (P) each have self-crosslinking properties.

<Compound (SC)>

The compound (SC) in the present embodiment is a compound represented by General Formula (sc-1).

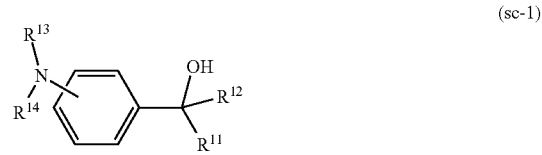

(sc-1)

[In the formula, $R^{11}$ and $R^{12}$ each independently are an organic group having 1 to 40 carbon atoms or a hydrogen atom. $R^{13}$ and $R^{14}$ each independently are an aromatic hydrocarbon group having 6 to 30 carbon atoms, which may have a substituent. Here, $R^{13}$ and $R^{14}$ may be bonded to each other to form a structure having an aromatic heterocyclic ring. In addition, a hydrogen atom of a phenylene group in the formula may be substituted with a substituent. * indicates a bond (hereinafter, the same shall apply in the present specification)].

In Formula (sc-1), and $R^{12}$ each independently are an organic group having 1 to 40 carbon atoms or a hydrogen atom.

Examples of the organic group for $R^{11}$ and $R^{12}$ include a monovalent hydrocarbon group which may have a substituent. The hydrocarbon group may be an aliphatic hydrocarbon group, or may be an aromatic hydrocarbon group, and is preferably an aromatic hydrocarbon group.

The number of carbon atoms of the aliphatic hydrocarbon group for $R^{11}$ and $R^{12}$ is preferably 1 to 40, more preferably 1 to 30, further more preferably 1 to 25, and particularly preferably 1 to 20.

The number of carbon atoms of the aromatic hydrocarbon group for $R^{11}$ and $R^{12}$ is preferably 6 to 30, more preferably 6 to 25, further more preferably 6 to 20, and particularly preferably 6 to 16.

The aromatic hydrocarbon group for $R^{11}$ and $R^{12}$ is a hydrocarbon group which has at least one aromatic ring. The aromatic ring is not particularly limited as long as it is a cyclic conjugated system having 4n+2π electrons, and may be monocyclic or polycyclic. Specific examples of the aromatic ring include aromatic hydrocarbon rings such as benzene, naphthalene, anthracene, phenanthrene, and pyrene.

In addition, the aromatic ring contained in the aromatic hydrocarbon group for $R^{11}$ and $R^{12}$ may be an aromatic heterocyclic ring in which a part of carbon atoms constituting the aromatic hydrocarbon ring is substituted with a hetero atom. Examples of the hetero atom in the aromatic heterocyclic ring include an oxygen atom, a sulfur atom, a nitrogen atom, and the like. Specific examples of the aromatic heterocyclic ring include a pyrrolidine ring, a pyridine ring, a thiophene ring, and the like.

Specific examples of the aromatic hydrocarbon group for $R^{11}$ and $R^{12}$ include a group (an aryl group or a heteroaryl group) obtained by removing one hydrogen atom from the aromatic hydrocarbon ring or the aromatic heterocyclic ring;

a group obtained by removing one hydrogen atom from an aromatic compound (for example, biphenyl, fluorene, and the like) containing two or more aromatic rings; a group (for example, an arylalkyl group such as benzyl group, phenethyl group, 1-naphthylmethyl group, 2-naphthylmethyl group, 1-naphthylethyl group, 2-naphthylethyl group, and the like) in which one of hydrogen atoms of the aromatic hydrocarbon ring or the aromatic heterocyclic ring is substituted with an alkylene group; and the like. The number of carbon atoms of the alkylene group bonded to the aromatic hydrocarbon ring or the aromatic heterocyclic ring is preferably 1 to 4, and more preferably 1 to 2.

Examples of the substituent that may be contained in a hydrocarbon group for $R^{11}$ and $R^{12}$ include a carbonyl group, an alkoxy group, a halogen atom, an alkyl group, an alkenyl group, an alkynyl group, and the like. The number of carbon atoms of the alkyl group, the alkenyl group, and the alkynyl group in the substituent is preferably 1 to 5, and more preferably 1 to 3.

Specific examples of the organic groups for $R^{11}$ and $R^{12}$ are shown below.

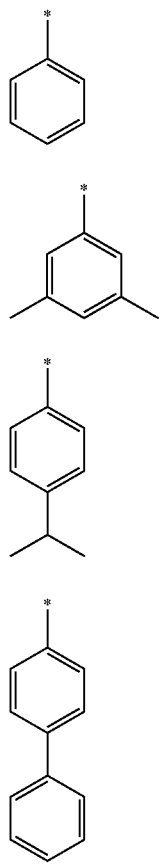

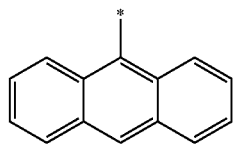

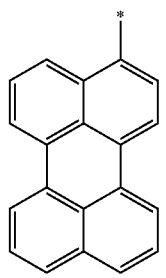

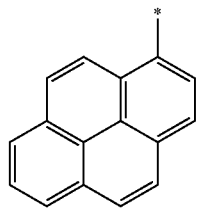

Among these, $R^{11}$ and $R^{12}$ are preferably aromatic hydrocarbon groups or hydrogen atoms which may have a substituent, and more preferably groups (aryl groups) obtained by removing one hydrogen atom from the aromatic hydrocarbon ring, or hydrogen atom.

In Formula (sc-1), $R^{13}$ and $R^{14}$ each independently are an aromatic hydrocarbon group having 6 to 30 carbon atoms, which may have a substituent.

The number of carbon atoms of the aromatic hydrocarbon group for $R^{13}$ and $R^{14}$ is 6 to 30, and preferably 6 to 25.

The aromatic hydrocarbon group for $R^{13}$ and $R^{14}$ is a hydrocarbon group which has at least one aromatic ring. The aromatic ring is not particularly limited as long as it is a cyclic conjugated system having $4n+2\pi$ electrons, and may be monocyclic or polycyclic.

Specific examples of the aromatic ring include an aromatic hydrocarbon ring such as benzene, naphthalene, anthracene, phenanthrene, pyrene, or the like; an aromatic heterocyclic ring in which a part of carbon atoms constituting the aromatic hydrocarbon ring is substituted with hetero atoms; and the like. Examples of the hetero atom in the aromatic heterocyclic ring include an oxygen atom, a sulfur atom, a nitrogen atom, and the like. Specific examples of the aromatic heterocyclic ring include a pyrrolidine ring, a pyridine ring, a thiophene ring, and the like.

Specific examples of the aromatic hydrocarbon group for $R^{13}$ and $R^{14}$ include a group (an aryl group or a heteroaryl group) obtained by removing one hydrogen atom from the aromatic hydrocarbon ring or the aromatic heterocyclic ring; a group obtained by removing one hydrogen atom from an aromatic compound (for example, biphenyl, fluorene, and the like) containing two or more aromatic rings; a group (for example, an arylalkyl group such as benzyl group, phenethyl group, 1-naphthylmethyl group, 2-naphthylmethyl group, 1-naphthylethyl group, 2-naphthylethyl group, and the like) in which one of hydrogen atoms of the aromatic hydrocarbon ring or the aromatic heterocyclic ring is substituted with an alkylene group; and the like. The number of carbon atoms of the alkylene group to be bonded to the aromatic hydrocarbon ring or the aromatic heterocyclic ring is preferably 1 to 4, and more preferably 1 to 2.

The aromatic hydrocarbon groups for $R^{13}$ and $R^{14}$ may have a substituent, or may not have a substituent. Examples of the substituent include a hydroxy group, a carbonyl group, an alkoxy group, a halogen atom, an alkyl group, an alkenyl group, an alkynyl group, and the like. The number of carbon atoms of the alkyl group, the alkenyl group, and the alkynyl group in the substituent is preferably 1 to 5, and more preferably 1 to 3. Preferred examples of the substituent include a linear or branched alkyl group having 1 to 3 carbon atoms. The aromatic hydrocarbon group for $R^{13}$ and $R^{14}$ is preferably a group having no substituent from a viewpoint of improving etching resistance.

Here, $R^{13}$ and $R^{14}$ in Formula (sc-1) may be bonded to each other to form a structure having an aromatic heterocyclic ring.

The hydrogen atom of the phenylene group in Formula (sc-1) may be substituted with a substituent. Examples of this substituent include a halogen atom and an alkyl group having 1 to 5 carbon atoms.

As the compound (SC), for example, a compound represented by General Formula (sc-1-1) is preferably exemplified.

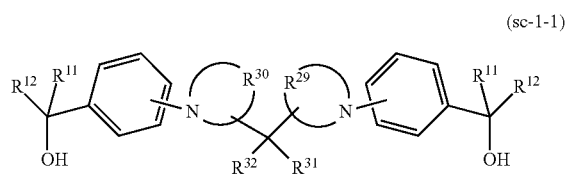

(sc-1-1)

[In the formula, a plurality of $R^{11}$ and $R^{12}$ each independently are an organic group having 1 to 40 carbon atoms or a hydrogen atom. $R^{29}$ is a group that forms an aromatic heterocyclic ring together with a nitrogen atom. $R^{30}$ is a group that forms an aromatic heterocyclic ring together with a nitrogen atom. $R^{31}$ and $R^{32}$ each independently are an aromatic hydrocarbon group having 6 to 30 carbon atoms, which may have a substituent, or a hydrogen atom. Here, $R^{31}$ and $R^{32}$ may be bonded to each other to form a structure having an aromatic ring. In addition, the hydrogen atom of the two phenylene groups in the formula may be substituted with a substituent].

In Formula (sc-1-1), the plurality of $R^{11}$ and $R^{12}$ each independently are an organic group having 1 to 40 carbon atoms or a hydrogen atom. The description of $R^{11}$ and $R^{12}$ here is the same as the description of $R^{11}$ and $R^{12}$ in Formula (sc-1).

In Formula (sc-1-1), $R^{29}$ is a group that forms an aromatic heterocyclic ring together with a nitrogen atom. $R^{30}$ is a group that forms an aromatic heterocyclic ring together with a nitrogen atom.

In Formula (sc-1-1), $R^{31}$ and $R^{32}$ each independently are an aromatic hydrocarbon group having 6 to 30 carbon atoms, which may have a substituent, or a hydrogen atom.

The description of the aromatic hydrocarbon group having 6 to 30 carbon atoms, which may have a substituent, for $R^{31}$ and $R^{32}$ is the same as the description of the aromatic hydrocarbon group having 6 to 30 carbon atoms, which may have a substituent, for $R^{13}$ and $R^{14}$ in Formula (sc-1).

Here, $R^{31}$ and $R^{32}$ in Formula (sc-1-1) may be bonded to each other to form a structure having an aromatic ring. Here, the structure having an aromatic ring may be a monocyclic ring or a polycyclic ring. Among these, polycyclic aromatic hydrocarbon groups are more preferable, and those having no substituents are further more preferable, since it is possible to improve etching resistance by increasing the carbon content.

In addition, the hydrogen atom of two phenylene groups in Formula (sc-1-1) may be substituted with a substituent. Examples of the substituent here include a halogen atom and an alkyl group having 1 to 5 carbon atoms.

Specific examples of the compound (SC) are shown below.

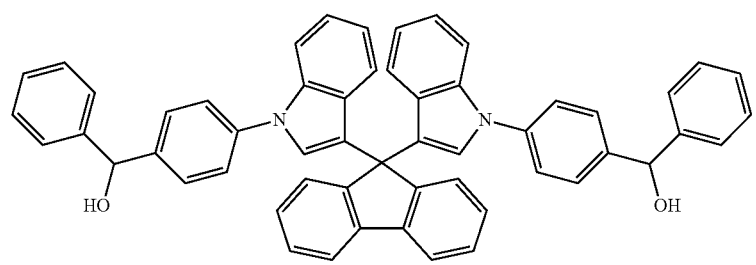

(sc-1-11)

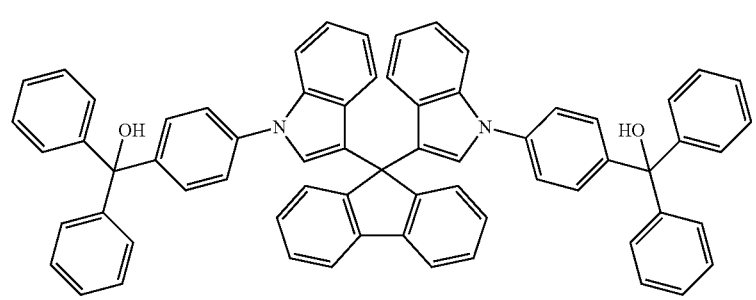

(sc-1-12)

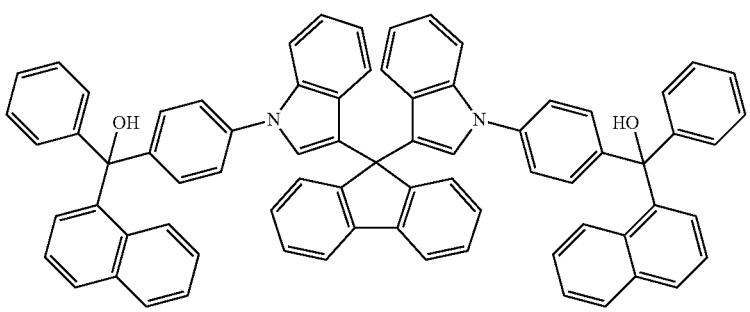
(sc-1-13)

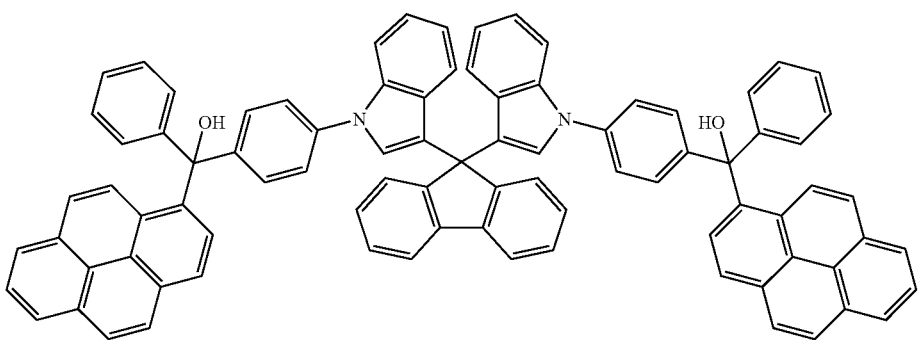
(sc-1-14)

In the hard-mask forming composition of the present embodiment, the compound (SC) may be used alone, or two or more compounds may be used in combination.

A molecular weight of the compound (SC) is preferably 700 or more, more preferably 900 to 4,000, and further more preferably 1,000 to 2,000. In a case where the molecular weight of the compound (SC) is set to be equal to or higher than the lower limit value of the preferable range, the etching resistance, solvent resistance, and heat resistance are more likely to be improved. In addition, outgassing is less likely to be generated during baking when processing the support. In a case where the baking temperature is adjusted to be equal to or less than the upper limit value of the preferable range, the compound (SC) can be easily dissolved in the solvent at a time of preparing the hard-mask forming composition.

A ratio of the compound (SC) in the film-forming component is preferably 50% by mass or more, more preferably 70% by mass or more, further more preferably 80% by mass or more, and even further more preferably 90% by mass or more, particularly preferably 95% by mass or more, and may be 100% by mass, based on the total mass of the film-forming component.

The ratio of the compound (SC) in the hard-mask forming composition is preferably 5% by mass to 30% by mass, more preferably 6% by mass to 25% by mass, and further more preferably 7% by mass to 20% by mass, based on the total mass of the hard-mask forming composition.

<Resin (P)>

The resin (P) in the present embodiment is a resin having a partial structure represented by General Formula (sc-p1).

The "partial structure" here means a structure that constitutes a part of the resin. This "partial structure" may constitute a part of the main chain or may constitute a side chain.

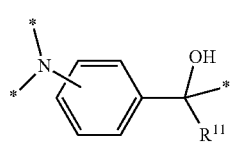
(sc-p1)

[In the formula, $R^{11}$ is an organic group having 1 to 40 carbon atoms or a hydrogen atom. The hydrogen atom of the phenylene group in the formula may be substituted with a substituent].

In Formula (sc-p1), $R^{11}$ is an organic group having 1 to 40 carbon atoms or a hydrogen atom. The description of $R^{11}$ here is the same as the description of $R^{11}$ in Formula (sc-1).

The hydrogen atom of the phenylene group in Formula (sc-p1) may be substituted with a substituent. Examples of the substituent here include a halogen atom and an alkyl group having 1 to 5 carbon atoms.

As the resin (P), for example, a resin having a structural unit (u11) represented by General Formula (u11-1) to be stated later is preferably exemplified.

Alternatively, as the resin (P), for example, a resin having a structural unit (u12) represented by General Formula (u12-1) to be stated later is preferably exemplified.

Alternatively, as the resin (P), for example, a resin having a structural unit (u13) represented by General Formula (u13-1) to be stated later is preferably exemplified.

<<Structural Unit (u11)>>

The structural unit (u11) is a structural unit represented by General Formula (u11-1).

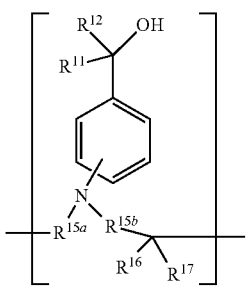

(u11-1)

[In the formula, $R^{11}$ and $R^{12}$ each independently are an organic group having 1 to 40 carbon atoms or a hydrogen atom. $R^{15a}$ and $R^{15b}$ each independently are an aromatic hydrocarbon group having 6 to 30 carbon atoms, which may have a substituent, or a hydrogen atom. Here, $R^{15a}$ and $R^{15b}$ may be bonded to each other to form a structure having an aromatic heterocyclic ring. $R^{16}$ and $R^{17}$ each independently are an aromatic hydrocarbon group having 6 to 30 carbon atoms, which may have a substituent, or a hydrogen atom. Here, $R^{16}$ and $R^{17}$ may be bonded to each other to form a structure having an aromatic ring. In addition, a hydrogen atom of a phenylene group in the formula may be substituted with a substituent].

In Formula (u11-1), $R^{11}$ and $R^{12}$ each independently are an organic group having 1 to 40 carbon atoms or a hydrogen atom.

Examples of the organic group for $R^{11}$ and $R^{12}$ here include a monovalent hydrocarbon group which may have a substituent. The hydrocarbon group may be an aliphatic hydrocarbon group, or may be an aromatic hydrocarbon group, and is preferably an aromatic hydrocarbon group.

The number of carbon atoms of the aliphatic hydrocarbon group for $R^{11}$ and $R^{12}$ is preferably 1 to 40, more preferably 1 to 30, further more preferably 1 to 25, and particularly preferably 1 to 20.

The number of carbon atoms of the aromatic hydrocarbon group for $R^{11}$ and $R^{12}$ is preferably 6 to 30, more preferably 6 to 25, further more preferably 6 to 20, and particularly preferably 6 to 16.

The aromatic hydrocarbon group for $R^{11}$ and $R^{12}$ is a hydrocarbon group which has at least one aromatic ring. The aromatic ring is not particularly limited as long as it is a cyclic conjugated system having $4n+2\pi$ electrons, and may be monocyclic or polycyclic. Specific examples of the aromatic ring include aromatic hydrocarbon rings such as benzene, naphthalene, anthracene, phenanthrene, and pyrene.

In addition, the aromatic ring contained in the aromatic hydrocarbon group for $R^{11}$ and $R^{12}$ may be an aromatic heterocyclic ring in which a part of carbon atoms constituting the aromatic hydrocarbon ring is substituted with a hetero atom. Examples of the hetero atom in the aromatic heterocyclic ring include an oxygen atom, a sulfur atom, a nitrogen atom, and the like. Specific examples of the aromatic heterocyclic ring include a pyrrolidine ring, a pyridine ring, a thiophene ring, and the like.

Specific examples of the aromatic hydrocarbon group for $R^{11}$ and $R^{12}$ include a group (an aryl group or a heteroaryl group) obtained by removing one hydrogen atom from the aromatic hydrocarbon ring or the aromatic heterocyclic ring; a group obtained by removing one hydrogen atom from an aromatic compound (for example, biphenyl, fluorene, and the like) containing two or more aromatic rings; a group (for example, an arylalkyl group such as benzyl group, phenethyl group, 1-naphthylmethyl group, 2-naphthylmethyl group, 1-naphthylethyl group, 2-naphthylethyl group, and the like) in which one of hydrogen atoms of the aromatic hydrocarbon ring or the aromatic heterocyclic ring is substituted with an alkylene group; and the like. The number of carbon atoms of the alkylene group bonded to the aromatic hydrocarbon ring or the aromatic heterocyclic ring is preferably 1 to 4, and more preferably 1 to 2.

Examples of the substituent that may be contained in a hydrocarbon group for $R^{11}$ and $R^{12}$ include a carbonyl group, an alkoxy group, a halogen atom, an alkyl group, an alkenyl group, an alkynyl group, and the like. The number of carbon atoms of the alkyl group, the alkenyl group, and the alkynyl group in the substituent is preferably 1 to 5, and more preferably 1 to 3.

Specific examples of the organic groups for $R^{11}$ and $R^{12}$ are shown below.

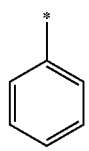

(org-1)

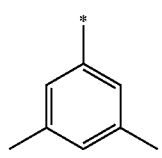

(org-2)

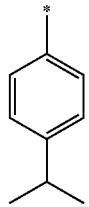

(org-3)

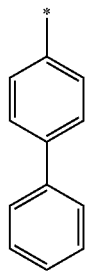

(org-4)

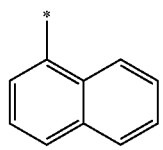

(org-5)

-continued

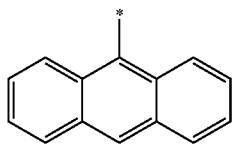
(org-6)

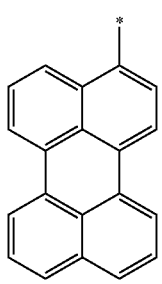
(org-7)

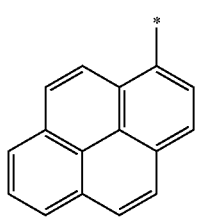
(org-8)

Among these, $R^{11}$ and $R^{12}$ are preferably aromatic hydrocarbon groups, which may have a substituent, or hydrogen atoms, and more preferably groups (aryl groups) obtained by removing one hydrogen atom from the aromatic hydrocarbon ring, or hydrogen atom.

In Formula (u11-1), $R^{15a}$ and $R^{15b}$ each independently are an aromatic hydrocarbon group having 6 to 30 carbon atoms, which may have a substituent, or a hydrogen atom.

The number of carbon atoms of the aromatic hydrocarbon group for $R^{15a}$ and $R^{15b}$ is 6 to 30, and preferably 6 to 25.

The aromatic hydrocarbon group for $R^{15a}$ and $R^{15b}$ is a hydrocarbon group which has at least one aromatic ring. The aromatic ring is not particularly limited as long as it is a cyclic conjugated system having $4n+2\pi$ electrons, and may be monocyclic or polycyclic.

Specific examples of the aromatic ring include an aromatic hydrocarbon ring such as benzene, naphthalene, anthracene, phenanthrene, pyrene, or the like; an aromatic heterocyclic ring in which a part of carbon atoms constituting the aromatic hydrocarbon ring is substituted with hetero atoms; and the like. Examples of the hetero atom in the aromatic heterocyclic ring include an oxygen atom, a sulfur atom, a nitrogen atom, and the like. Specific examples of the aromatic heterocyclic ring include a pyrrolidine ring, a pyridine ring, a thiophene ring, and the like.

Specific examples of the aromatic hydrocarbon group for $R^{15a}$ and $R^{15b}$ include a group (an aryl group or a heteroaryl group) obtained by removing one hydrogen atom from the aromatic hydrocarbon ring or the aromatic heterocyclic ring; a group obtained by removing one hydrogen atom from an aromatic compound (for example, biphenyl, fluorene, and the like) containing two or more aromatic rings; a group (for example, an arylalkyl group such as benzyl group, phenethyl group, 1-naphthylmethyl group, 2-naphthylmethyl group, 1-naphthylethyl group, 2-naphthylethyl group, and the like) in which one of hydrogen atoms of the aromatic hydrocarbon ring or the aromatic heterocyclic ring is substituted with an alkylene group; and the like. The number of carbon atoms of the alkylene group to be bonded to the aromatic hydrocarbon ring or the aromatic heterocyclic ring is preferably 1 to 4, and more preferably 1 to 2.

The aromatic hydrocarbon groups for $R^{15a}$ and $R^{15b}$ may have a substituent, or may not have a substituent. Examples of the substituent include a hydroxy group, a carbonyl group, an alkoxy group, a halogen atom, an alkyl group, an alkenyl group, an alkynyl group, and the like. The number of carbon atoms of the alkyl group, the alkenyl group, and the alkynyl group in the substituent is preferably 1 to 5, and more preferably 1 to 3. Preferred examples of the substituent include a linear or branched alkyl group having 1 to 3 carbon atoms. The aromatic hydrocarbon group for $R^{15a}$ and $R^{15b}$ is preferably a group having no substituent from a viewpoint of improving etching resistance.

Here, $R^{15a}$ and $R^{15b}$ in Formula (u11-1) may be bonded to each other to form a structure having an aromatic heterocyclic ring. The structure having an aromatic heterocyclic ring here may be a monocyclic ring or a polycyclic ring.

In Formula (u11-1), $R^{16}$ and $R^{17}$ each independently are an aromatic hydrocarbon group having 6 to 30 carbon atoms, which may have a substituent, or a hydrogen atom.

The description of the aromatic hydrocarbon group having 6 to 30 carbon atoms which may have a substituent for $R^{16}$ and $R^{17}$ is the same as the description of the aromatic hydrocarbon group having 6 to 30 carbon atoms which may have a substituent for $R^{15a}$ and $R^{15b}$ in Formula (u11-1).

Here, $R^{16}$ and $R^{17}$ in Formula (u11-1) may be bonded to each other to form a structure having an aromatic ring. Here, the structure having an aromatic ring may be a monocyclic ring or a polycyclic ring. Among these, polycyclic aromatic hydrocarbon groups are more preferable, and those having no substituents are further more preferable, since it is possible to improve etching resistance by increasing the carbon content.

The hydrogen atom of the phenylene group in Formula (u11-1) may be substituted with a substituent. Examples of this substituent include a halogen atom and an alkyl group having 1 to 5 carbon atoms.

Specific examples of the structural unit (u11) are shown below.

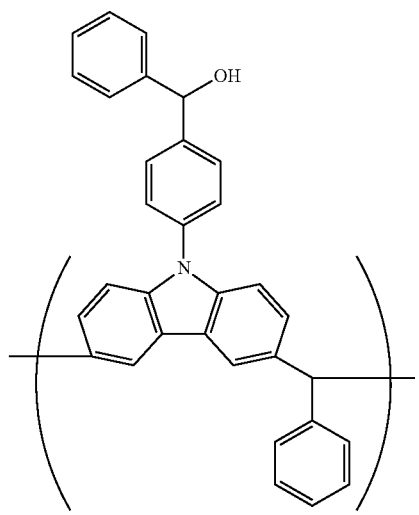
(u11-1-1)

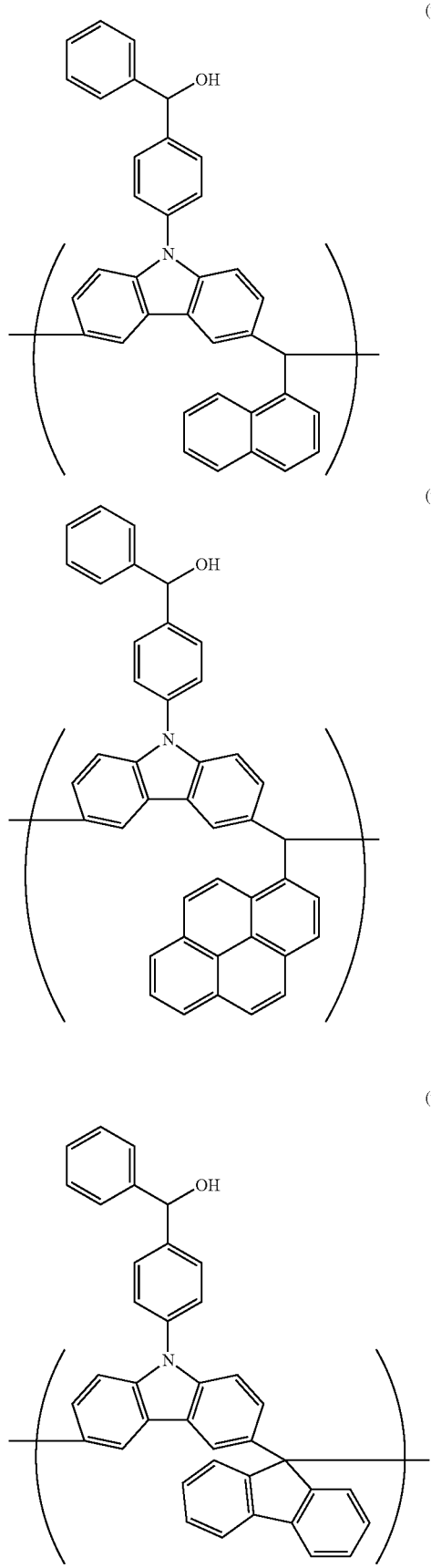
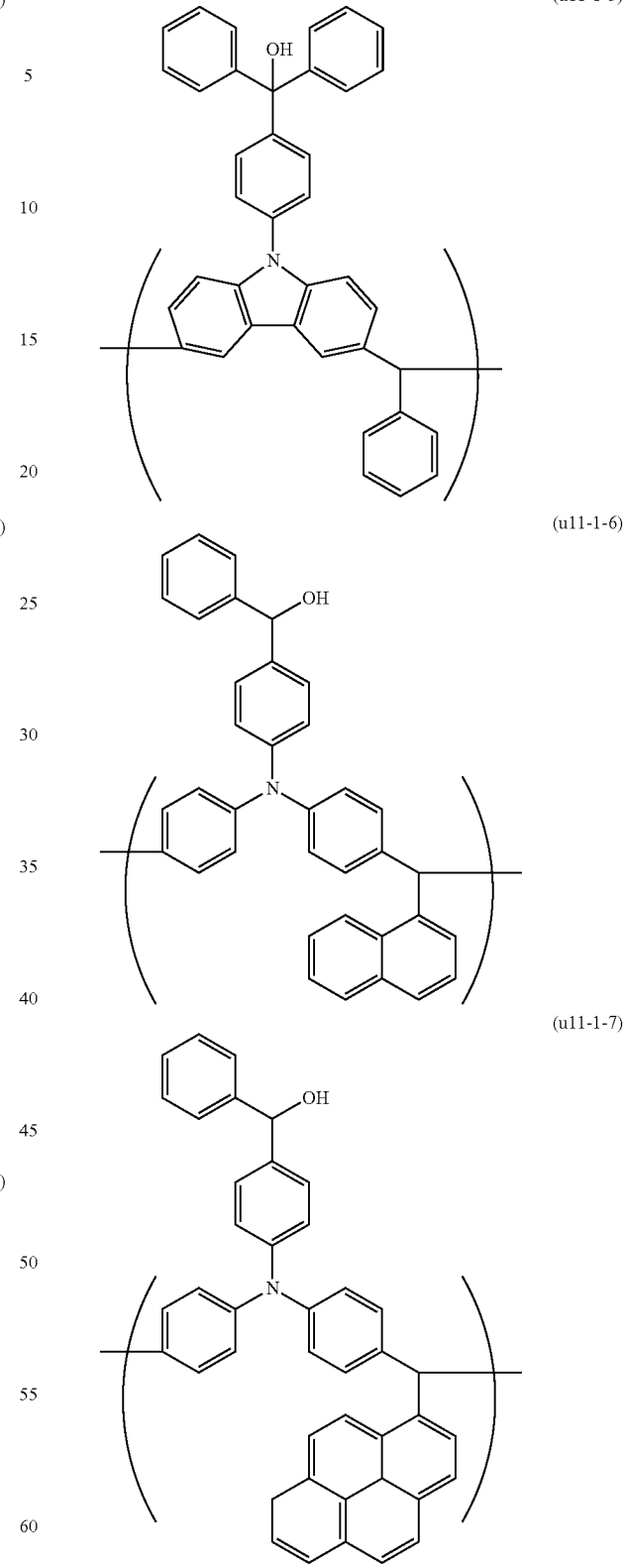
The structural unit (u11) of the resin (P) may be one type, or may be two or more types.
The ratio of the structural unit (u11) in the resin (P) is preferably 50 mol % or more, more preferably 70 mol % or more, further more preferably 80 mol % or more, and particularly preferably 90 mol % or more, based on the total sum (100 mol %) of all the structural units constituting the resin (P), and may be 100 mol %.

In a case where the ratio of the structural unit (u11) is set to be equal to or higher than the lower limit value of the preferable range, the etching resistance is more likely to be increased, and the solvent resistance and the heat resistance are improved.

<<Structural Unit (u12)>>

The structural unit (u12) is a structural unit represented by General Formula (u12-1).

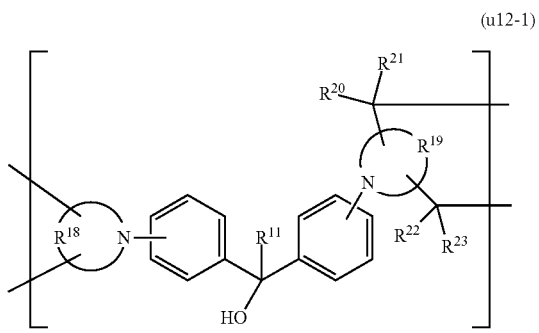

(u12-1)

[In the formula, $R^{11}$ is an organic group having 1 to 40 carbon atoms or a hydrogen atom. $R^{18}$ is a group that forms an aromatic heterocyclic ring together with a nitrogen atom. $R^{19}$ is a group that forms an aromatic heterocyclic ring together with a nitrogen atom. $R^{20}$ and $R^{21}$ each independently are an aromatic hydrocarbon group having 6 to 30 carbon atoms, which may have a substituent, or a hydrogen atom. Here, $R^{20}$ and $R^{21}$ may be bonded to each other to form a structure having an aromatic ring. $R^{22}$ and $R^{23}$ each independently are an aromatic hydrocarbon group having 6 to 30 carbon atoms, which may have a substituent, or a hydrogen atom. Here, $R^{22}$ and $R^{23}$ may be bonded to each other to form a structure having an aromatic ring. In addition, the hydrogen atom of the two phenylene groups in the formula may be substituted with a substituent].

In Formula (u12-1), $R^{11}$ is an organic group having 1 to 40 carbon atoms or a hydrogen atom. The description of $R^{11}$ here is the same as the description of $R^{11}$ in Formula (u11-1).

In Formula (u12-1), $R^{18}$ is a group that forms an aromatic heterocyclic ring together with a nitrogen atom. $R^{19}$ is a group that forms an aromatic heterocyclic ring together with a nitrogen atom.

In Formula (u12-1), $R^{20}$ and $R^{21}$ each independently are an aromatic hydrocarbon group having 6 to 30 carbon atoms, which may have a substituent, or a hydrogen atom.

The description of the aromatic hydrocarbon group having 6 to 30 carbon atoms, which may have a substituent, for $R^{20}$ and $R^{21}$ is the same as the description of the aromatic hydrocarbon group having 6 to 30 carbon atoms, which may have a substituent, for $R^{15a}$ and $R^{15b}$ in Formula (u11-1).

Here, $R^{20}$ and $R^{21}$ in Formula (u12-1) may be bonded to each other to form a structure having an aromatic ring. Here, the structure having an aromatic ring may be a monocyclic ring or a polycyclic ring. Among these, polycyclic aromatic hydrocarbon groups are more preferable, and those having no substituents are further more preferable, since it is possible to improve etching resistance by increasing the carbon content.

In Formula (u12-1), $R^{22}$ and $R^{23}$ each independently are an aromatic hydrocarbon group having 6 to 30 carbon atoms, which may have a substituent, or a hydrogen atom.

The description of the aromatic hydrocarbon group having 6 to 30 carbon atoms, which may have a substituent, for $R^{22}$ and $R^{23}$ is the description of the aromatic hydrocarbon group having 6 to 30 carbon atoms, which may have a substituent, for $R^{15a}$ and $R^{15b}$ in Formula (u11-1).

Here, $R^{22}$ and $R^{23}$ in Formula (u12-1) may be bonded to each other to form a structure having an aromatic ring. Here, the structure having an aromatic ring may be a monocyclic ring or a polycyclic ring. Among these, polycyclic aromatic hydrocarbon groups are more preferable, and those having no substituents are further more preferable, since it is possible to improve etching resistance by increasing the carbon content.

The hydrogen atom of the two phenylene groups in Formula (u12-1) may be substituted with a substituent. Examples of this substituent include a halogen atom and an alkyl group having 1 to 5 carbon atoms.

Specific examples of the structural unit (u12) are shown below.

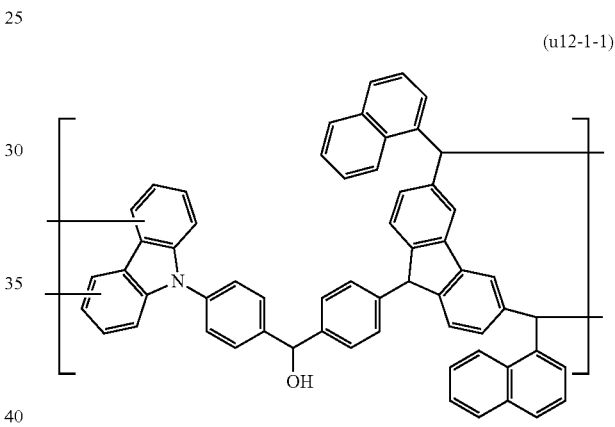

(u12-1-1)

The structural unit (u12) of the resin (P) may be one type, or may be two or more types.

A ratio of the structural unit (u12) in the resin (P) is preferably 50 mol % or more, more preferably 70 mol % or more, further more preferably 80 mol % or more, and particularly preferably 90 mol % or more, based on the total sum (100 mol %) of all the structural units constituting the resin (P), and may be 100 mol %.

In a case where the ratio of the structural unit (u12) is set to be equal to or higher than the lower limit value of the preferable range, the etching resistance is more likely to be increased, and the solvent resistance and the heat resistance are improved.

<<Structural Unit (u13)>>

The structural unit (u13) is a structural unit represented by General Formula (u13-1).

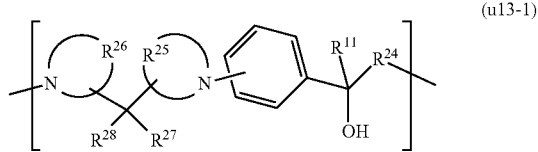

(u13-1)

[In the formula, $R^{11}$ is an organic group having 1 to 40 carbon atoms or a hydrogen atom. $R^{24}$ is an organic group having 1 to 40 carbon atoms. $R^{25}$ is a group that forms an aromatic heterocyclic ring together with a nitrogen atom. $R^{26}$ is a group that forms an aromatic heterocyclic ring together with a nitrogen atom. $R^{27}$ and $R^{28}$ each independently are an aromatic hydrocarbon group having 6 to 30 carbon atoms, which may have a substituent, or a hydrogen atom. Here, $R^{27}$ and $R^{28}$ may be bonded to each other to form a structure having an aromatic ring. In addition, a hydrogen atom of a phenylene group in the formula may be substituted with a substituent].

In Formula (u13-1), $R^{11}$ is an organic group having 1 to 40 carbon atoms or a hydrogen atom. The description of $R^{11}$ here is the same as the description of $R^{11}$ in Formula (u11-1).

In Formula (u13-1), $R^{24}$ is an organic group having 1 to 40 carbon atoms.

The organic group for $R^{24}$ here includes a divalent hydrocarbon group which may have a substituent. The hydrocarbon group may be an aliphatic hydrocarbon group, or may be an aromatic hydrocarbon group, and is preferably an aromatic hydrocarbon group.

The number of carbon atoms of the aliphatic hydrocarbon group for $R^{24}$ is preferably 1 to 40, more preferably 1 to 30, further more preferably 1 to 25, and particularly preferably 1 to 20.

The number of carbon atoms of the aromatic hydrocarbon group for $R^{24}$ is preferably 6 to 30, more preferably 6 to 25, further more preferably 6 to 20, and particularly preferably 6 to 16.

The aromatic hydrocarbon group for $R^{24}$ is a hydrocarbon group which has at least one aromatic ring. The aromatic ring is not particularly limited as long as it is a cyclic conjugated system having $4n+2\pi$ electrons, and may be monocyclic or polycyclic. Specific examples of the aromatic ring include aromatic hydrocarbon rings such as benzene, naphthalene, anthracene, phenanthrene, and pyrene.

In addition, in the aromatic ring of the aromatic hydrocarbon group for $R^{24}$, a part of carbon atoms constituting the aromatic hydrocarbon ring may be an aromatic heterocyclic ring substituted with a hetero atom. Examples of the hetero atom in the aromatic heterocyclic ring include an oxygen atom, a sulfur atom, a nitrogen atom, and the like. Specific examples of the aromatic heterocyclic ring include a pyrrolidine ring, a pyridine ring, a thiophene ring, and the like.

Specific examples of the aromatic hydrocarbon group for $R^{24}$ include a group (an arylene group or a heteroarylene group) obtained by removing two hydrogen atoms from the aromatic hydrocarbon ring or the aromatic heterocyclic ring; a group obtained by removing two hydrogen atoms from an aromatic compound (for example, biphenyl, fluorene, and the like) containing two or more aromatic rings; a group (for example, an arylalkyl group such as benzyl group, phenethyl group, 1-naphthylmethyl group, 2-naphthylmethyl group, 1-naphthylethyl group, 2-naphthylethyl group, and the like) in which one of hydrogen atoms of the aromatic hydrocarbon ring or the aromatic heterocyclic ring is substituted with an alkylene group; and the like. The number of carbon atoms of the alkylene group bonded to the aromatic hydrocarbon ring or the aromatic heterocyclic ring is preferably 1 to 4, and more preferably 1 to 2.

Examples of the substituent of the hydrocarbon group for $R^{24}$ include a carbonyl group, an alkoxy group, a halogen atom, an alkyl group, an alkenyl group, an alkynyl group, and the like. The number of carbon atoms of the alkyl group, the alkenyl group, and the alkynyl group in the substituent is preferably 1 to 5, and more preferably 1 to 3.

Specific examples of the organic group for $R^{24}$ are shown below.

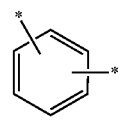

(org-21)

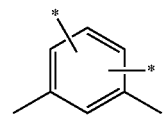

(org-22)

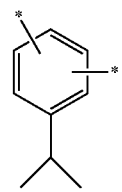

(org-23)

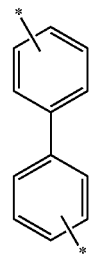

(org-24)

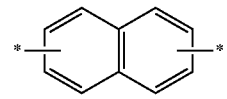

(org-25)

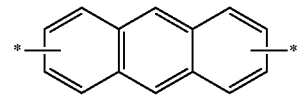

(org-26)

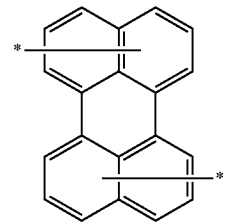

(org-27)

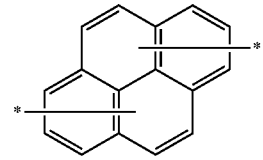

(org-28)

Among these, $R^{24}$ is preferably an aromatic hydrocarbon group, which may have a substituent, or a hydrogen atom, and more preferably a group (arylene group) obtained by removing two hydrogen atoms from an aromatic hydrocarbon ring, or a hydrogen atom.

In Formula (u13-1), $R^{25}$ is a group that forms an aromatic heterocyclic ring together with a nitrogen atom. $R^{26}$ is a group that forms an aromatic heterocyclic ring together with a nitrogen atom.

In Formula (u13-1), $R^{27}$ and $R^{28}$ each independently are an aromatic hydrocarbon group having 6 to 30 carbon atoms, which may have a substituent, or a hydrogen atom.

The description of the aromatic hydrocarbon group having 6 to 30 carbon atoms which may have a substituent for $R^{27}$ and $R^{28}$ is the same as the description of the aromatic hydrocarbon group having 6 to 30 carbon atoms, which may have a substituent, for $R^{15a}$ and $R^{15b}$ in Formula (u11-1).

Here, $R^{27}$ and $R^{28}$ in Formula (u13-1) may be bonded to each other to form a structure having an aromatic ring. Here, the structure having an aromatic ring may be a monocyclic ring or a polycyclic ring. Among these, polycyclic aromatic hydrocarbon groups are more preferable, and those having no substituents are further more preferable, since it is possible to improve etching resistance by increasing the carbon content.

The hydrogen atom of the phenylene group in Formula (u13-1) may be substituted with a substituent. Examples of this substituent include a halogen atom and an alkyl group having 1 to 5 carbon atoms.

Specific examples of the structural unit (u13) are shown below.

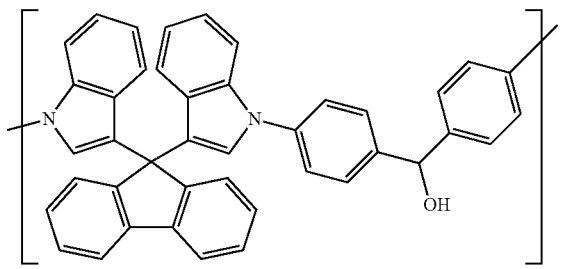

(u13-1-1)

The structural unit (u13) of the resin (P) may be one type, or may be two or more types.

A ratio of the structural unit (u13) in the resin (P) is preferably 50 mol % or more, more preferably 70 mol % or more, further more preferably 80 mol % or more, and particularly preferably 90 mol % or more, based on the total sum (100 mol %) of all the structural units constituting the resin (P), and may be 100 mol %.

In a case where the ratio of the structural unit (u13) is set to be equal to or higher than the lower limit value of the preferable range, the etching resistance is more likely to be increased, and the solvent resistance and the heat resistance are improved.

The resin (P) may have other structural units in addition to the above-mentioned structural unit (u11), structural unit (u12), or structural unit (u13).

As the other structural unit, for example, a structural unit having a high carbon content is preferable from a viewpoint of etching resistance, and the structural unit containing an aromatic hydrocarbon group (excluding any one of the structural units (u11) to (u13)) and the like are exemplified.

A weight average molecular weight (Mw) (based on polystyrene conversion by gel permeation chromatography (GPC)) of the resin (P) is not particularly limited, and is preferably 1,000 to 50,000, more preferably 1,500 to 20,000, and further more preferably 2,000 to 10,000. In a case where Mw of the resin (P) is within the preferable range, the etching resistance and the heat resistance are more easily improved.

A dispersion degree (Mw/Mn) of the resin (P) is not particularly limited, and is preferably about 1.0 to 4.0, more preferably about 1.0 to 3.0, and further more preferably about 1.0 to 2.5. Mn represents a number average molecular weight.

In the hard-mask forming composition of the present embodiment, the resin (P) may be used alone, or two or more types thereof may be used in combination.

A ratio of the resin (P) in the film-forming component is preferably 50% by mass or more, more preferably 70% by mass or more, further more preferably 80% by mass or more, even further more preferably 90% by mass or more, and particularly preferably 95% by mass or more, based on the total mass of the film-forming component, and may be 100% by mass.

A ratio of the resin (P) in the hard-mask forming composition is preferably 5% to 30% by mass, more preferably 6% to 25% by mass, and further more preferably 7% to 20% by mass, based on the total mass of the hard-mask forming composition.

Examples of the film-forming component in the hard-mask forming composition of the present embodiment preferably include the compound (SC); a resin having the structural unit (u11), a resin having the structural unit (u12), and a resin having the structural unit (u13).

Specific examples of these resins include a polymer having a repeating structure of the structural unit (u11), a polymer having a repeating structure of the structural unit (u12), and a polymer having a repeating structure of the structural unit (u13).

In the hard-mask forming composition of the present embodiment, only the compound (SC) stated above may be used, only the resin (P) may be used, or the compound (SC) may be used as the film-forming component. The compound (SC) and the resin (P) may be used in combination. Alternatively, as the film-forming component, in addition to at least one of the compound (SC) and the resin (P), a component having a film-forming performance other than these may be used in combination.

The above-mentioned component having a film-forming performance is not particularly limited, and may be optionally selected and used from a large number of those known in the related art as a base component of the hard mask layer.

In the hard-mask forming composition of the present embodiment, the content of the film-forming component may be appropriately adjusted according to a thickness of the hard mask layer to be formed and the like.

<Optional Components>

The hard-mask forming composition of the present embodiment may contain other components in addition to the compound (SC) and the resin (P) stated above.

Examples of the other components include a thermal acid generator component, a surfactant, a crosslinking agent, a crosslinking acceleration catalyst, a photoacid generator, an absorbent, a rheology modifier, an adhesion aider, a solvent, and the like.

<<Thermal Acid Generator Component>>

The hard-mask forming composition of the present embodiment preferably further contains a thermal acid generator component (hereinafter, also referred to as "(T) component") in addition to at least one of the compound (SC) and the resin (P).

Examples of the component (T) include perfluoroalkyl sulfonates (trifluoromethane sulfonate, perfluorobutane sulfonate, and the like), hexafluorophosphate, boron trifluoride salt, boron trifluoride ether complex, and the like.

Examples of preferable components (T) include a compound (T1) (hereinafter, referred to as "(T1) component") consisting of a cationic part and an anionic part represented by General Formula (T-1) and a compound (T2) (hereinafter, referred to as "(T2) component") consisting of a cationic part and an anionic part represented by General Formula (T-2).

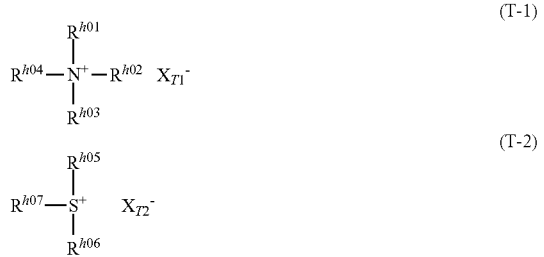

(T-1)

(T-2)

[In Formula (T-1), $R^{h01}$ to $R^{h04}$ each independently are a group selected from the group consisting of a hydrogen atom, an alkyl group having 1 to 20 carbon atoms, and an aryl group, and at least one of $R^{h01}$ to $R^{h04}$ is an aryl group. The alkyl group or aryl group may have a substituent. $X_{T1}^-$ is a counter anion. In Formula (T-2), $R^{h05}$ to $R^{h07}$ each independently are a group selected from the group consisting of an alkyl group having 1 to 20 carbon atoms and an aryl group, and at least one of $R^{h05}$ to $R^{h07}$ is an aryl group. The alkyl group or aryl group may have a substituent. $X_{T2}^-$ is a counter anion].

Regarding Anionic Part of Component (T1) and Component (T2)

Examples of $X_{T1}^-$ in Formula (T-1) and $X_{T2}^-$ in Formula (T-2) include a hexafluorophosphate anion, a perfluoroalkyl sulfonate anion (trifluoromethane sulfonate anion, perfluorobutane sulfonate anion, and the like), a tetrakis(pentafluorophenyl) borate anion, and the like.

Among these, a perfluoroalkyl sulfonate anion is preferable, a trifluoromethane sulfonate anion or a perfluorobutane sulfonate anion is more preferable, and a trifluoromethane sulfonate anion is further more preferable.

Regarding Cationic Part of Component (T1)

In Formula (T-1), the number of carbon atoms of the alkyl group for $R^{h01}$ to $R^{h04}$ is 1 to 20, preferably 1 to 10, and more preferably 1 to 5, and a linear or branched alkyl group having 1 to 5 carbon atoms is further more preferable. Specific examples thereof include a methyl group, an ethyl group, a propyl group, an isopropyl group, an n-butyl group, an isobutyl group, a tert-butyl group, a pentyl group, an isopentyl group, a neopentyl group, and the like. Among these, a methyl group and an ethyl group are preferable.

The alkyl group for $R^{h01}$ to $R^{h04}$ may have a substituent. Examples of the substituent include an alkoxy group, a halogen atom, a halogenated alkyl group, a hydroxyl group, a carbonyl group, a nitro group, an amino group, a cyclic group, and the like.

The alkoxy group as the substituent of the alkyl group is preferably an alkoxy group having 1 to 5 carbon atoms, more preferably a methoxy group, an ethoxy group, an n-propoxy group, an iso-propoxy group, an n-butoxy group or a tert-butoxy group, and further more preferably a methoxy group and an ethoxy group. Examples of the halogen atom as the substituent of the alkyl group include a fluorine atom, a chlorine atom, a bromine atom, an iodine atom, and the like, and the fluorine atom is preferable.

Examples of the halogenated alkyl group as the substituent of the alkyl group include an alkyl group having 1 to 5 carbon atoms, for example, a group in which a part or all of hydrogen atoms such as methyl group, ethyl group, propyl group, n-butyl group, and tert-butyl group is substituted with a halogen atom.

A carbonyl group as the substituent of the alkyl group is a group (>C=O) that substitutes a methylene group (—CH$_2$—) constituting the alkyl group.

Examples of the cyclic group as the substituent of the alkyl group include an aromatic hydrocarbon group and an alicyclic hydrocarbon group (which may be polycyclic or monocyclic). Examples of the aromatic hydrocarbon group here include the same as the aryl group for $R^{h01}$ to $R^{h04}$ to be stated later. In the alicyclic hydrocarbon group here, as the monocyclic alicyclic hydrocarbon group, a group obtained by removing one or more hydrogen atoms from a monocycloalkane is preferable. As the monocycloalkane, those having 3 to 6 carbon atoms are preferable, and specific examples thereof include cyclopentane, cyclohexane, and the like. In addition, as the polycyclic alicyclic hydrocarbon group, a group obtained by removing one or more hydrogen atoms from polycycloalkane is preferable, and as the polycycloalkane, those having 7 to 30 carbon atoms are preferable. Among these, as the polycycloalkane, a polycycloalkane having a polycyclic skeleton of a crosslinking ring system such as adamantane, norbornane, isobornane, tricyclodecane, and tetracyclododecane; and a polycycloalkane having a polycyclic skeleton of a condensed ring system such as a cyclic group having a steroid skeleton are more preferable.

In Formula (T-1), the aryl group for $R^{h01}$ to $R^{h04}$ is a hydrocarbon group having at least one aromatic ring.

The aromatic ring is not particularly limited as long as it is a cyclic conjugated system having 4n+2π electrons, and may be monocyclic or polycyclic. The number of carbon atoms of the aromatic ring is preferably 5 to 30, more preferably 5 to 20, further more preferably 6 to 15, and particularly preferably 6 to 12. Specific examples of the aromatic ring include an aromatic hydrocarbon ring such as benzene, naphthalene, anthracene, and phenanthrene; an aromatic heterocyclic ring in which a part of carbon atoms constituting the aromatic hydrocarbon ring is substituted with hetero atoms; and the like. Examples of the hetero atom in the aromatic heterocyclic ring include an oxygen atom, a sulfur atom, a nitrogen atom, and the like. Specific examples of the aromatic heterocyclic ring include a pyridine ring, a thiophene ring, and the like.

Specific examples of the aryl group for $R^{h01}$ to $R^{h04}$ include a group obtained by removing one hydrogen atom from the aromatic hydrocarbon ring or aromatic heterocyclic ring; a group obtained by removing one hydrogen atom from an aromatic compound (for example, biphenyl, fluorene, and the like) containing two or more aromatic rings; a group in which one hydrogen atom of the aromatic hydrocarbon ring or aromatic heterocyclic ring is substituted with an alkylene group (for example, arylalkyl group such as benzyl group, phenethyl group, 1-naphtylmethyl group, 2-naphtylmethyl group, 1-naphtylethyl group, 2-naphtylethyl group, and the like), and the like. The number of carbon atoms of an alkylene group to be bonded to the aromatic hydrocarbon ring or the aromatic heterocyclic ring is preferably 1 to 4, more preferably has 1 to 2, and particularly preferably 1. Among these, a group obtained by removing one hydrogen atom from the aromatic hydrocarbon ring or aromatic heterocyclic ring, and a group in which one hydrogen atoms of the aromatic hydrocarbon ring or aromatic heterocyclic ring is substituted with an alkylene group are more preferable, and a group obtained by removing one hydrogen atom from the aromatic hydrocarbon ring, and a group in which one hydrogen atom of the aromatic hydrocarbon ring is substituted with an alkylene group are further more preferable.

The aryl group for $R^{h01}$ to $R^{h04}$ may have a substituent. Examples of the substituent include an alkyl group, an alkoxy group, a halogen atom, a halogenated alkyl group, a hydroxyl group, a carbonyl group, a nitro group, an amino group, a cyclic group, an alkylcarbonyloxy group, and the like.

The alkyl group as the substituent of the aryl group is preferably an alkyl group having 1 to 5 carbon atoms, and preferably a methyl group, an ethyl group, a propyl group, an n-butyl group, and a tert-butyl group.

The description of the alkoxy group, the halogen atom, the halogenated alkyl group, the carbonyl group, and the cyclic group as the substituent of the aryl group is the same as the description of the alkoxy group, the halogen atom, the halogenated alkyl group, the carbonyl group, and the cyclic group as the substituent of the alkyl group stated above.

In the alkylcarbonyloxy group as a substituent of the aryl group, the number of carbon atoms of the alkyl part is preferably 1 to 5, examples of the alkyl part include a methyl group, an ethyl group, a propyl group, an isopropyl group, and the like, and among these, a methyl group and an ethyl group are preferable, and a methyl group is more preferable.

Here, in Formula (T1), at least one of $R^{h01}$ to $R^{h04}$ is an aryl group which may have a substituent.

Hereinafter, preferable cations as the cationic part of the component (T1) are shown below.

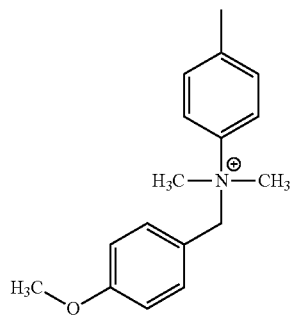
(T-ca-1-1)

Regarding Cationic Part of Component (T2)

In Formula (T-2), the description of the alkyl group and the aryl group for $R^{h05}$ to $R^{h07}$ is the same as the description of the alkyl group and the aryl group for $R^{h01}$ to $R^{h04}$ stated above, respectively.

Here, in Formula (T-2), at least one of $R^{h05}$ to $R^{h07}$ is an aryl group which may have a substituent.

Hereinafter, preferable cations as the cationic part of the component (T2) are shown below.

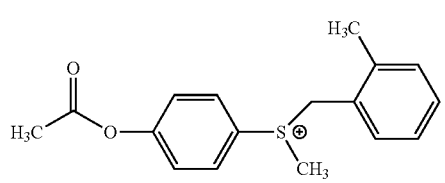
(T-ca-2-1)

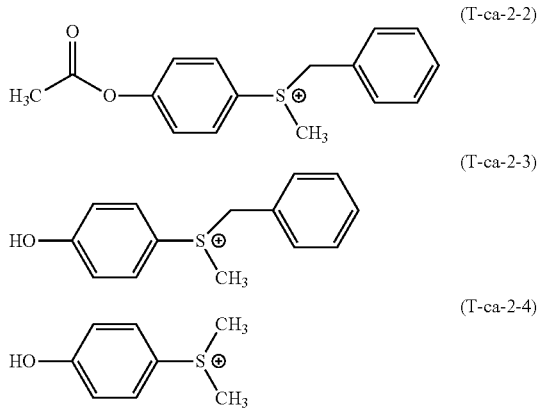
(T-ca-2-2)
(T-ca-2-3)
(T-ca-2-4)

The component (T) contained in the hard-mask forming composition of the present embodiment may be one type, or may be two or more types.

Among these, the hard-mask forming composition of the present embodiment preferably contains the component (T1).

As the component (T1), for example, a commercially available product having a product name of TAG-2689 (manufactured by KING INDUSTRY) may be used.

In a case where the hard-mask forming composition of the present embodiment contains the component (T), a content of the component (T) is preferably 0.01 to 20 parts by mass, more preferably 0.1 to 10 parts by mass, and further more preferably 0.5 to 5 parts by mass, based on 100 parts by mass of the total amount of the film-forming component. In a case where the content of the component (T) is within the preferable range, the reactivity of the crosslinking reaction in the compound (SC) or the resin (P) is further enhanced, and the etching resistance, the solvent resistance, and the heat resistance are further improved.

<<Surfactant>>

The hard-mask forming composition of the present embodiment may further contain a surfactant.

Examples of the surfactant include a nonionic surfactant encompassing: polyoxyethylene alkyl ethers such as polyoxyethylene lauryl ether, polyoxyethylene stearyl ether, polyoxyethylene cetyl ether, polyoxyethylene oleyl ether, and the like; polyoxyethylene alkyl allyl ethers such as polyoxyethylene octyl phenol ether, polyoxyethylene nonyl phenol ether, and the like; polyoxyethylene-polyoxypropylene block copolymers; sorbitan fatty acid esters such as sorbitan monolaurate, sorbitan monopalmitate, sorbitan monostearate, sorbitan monooleate, sorbitan trioleate, sorbitan tristearate, and the like; and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate, and the like; fluorinated surfactants such as F-top [registered trademark] EF 301, EF 303, and EF 352 [manufactured by Mitsubishi Materials Electronic Chemicals Co., Ltd. (formerly Tochem Products), product name], Megafac [registered trademark] F171, F173, R-30, and R-40 [manufactured by DIC Corporation (formerly Dai Nippon Ink Co., Ltd.), product name], Fluorad FC430 and FC431 (manufactured by Sumitomo 3M Co., Ltd., product name), Asahi Guard [registered trademark] AG710, Surflon [registered trademark] S-382, SC101, SC102, SC103, SC104, SC105, and SC106 (manufactured by Asahi Glass Co., Ltd., product name); Organosiloxane Polymer KP341 (manufactured by Shin-Etsu Chemical Co., Ltd.); and the like.

The surfactant contained in the hard-mask forming composition of the present embodiment may be one type, or two or more types.

Among these, the hard-mask forming composition of the present embodiment preferably contains a fluorinated surfactant.

In a case where the hard-mask forming composition of the present embodiment contains a surfactant, a content of the surfactant is preferably 0.01 to 10 parts by mass, more preferably 0.01 to 5 parts by mass, and further more preferably 0.05 to 1 part by mass, based on 100 parts by mass of the total amount of the film-forming component. In a case where the content of the surfactant is within the preferable range, a film surface when applying the hard-mask forming composition is made uniform, and striations (application defects such as wavy pattern and striped pattern) can be further prevented.

<<Crosslinking Agent>>

Examples of the crosslinking agent include an amino-based crosslinking agent such as glycoluryl having a methylol group or an alkoxymethyl group; a melamine-based crosslinking agent; and the like. Specific examples of the crosslinking agent include Nikalac [registered trademark] series (Nikalac MX270 and the like) manufactured by Sanwa Chemical Co., Ltd. The crosslinking agent may be used alone, or two or more types thereof may be used in combination.

<<Crosslinking Acceleration Catalyst>>

Examples of the crosslinking acceleration catalyst include acidic compounds such as p-toluenesulfonic acid, trifluoromethanesulfonic acid, pyridinium p-toluenesulfonic acid, salicylic acid, sulfosalicylic acid, citric acid, benzoic acid, hydroxybenzoic acid, naphthalenecarboxylic acid, and the like. The crosslinking acceleration catalyst may be used alone, or two or more types thereof may be used in combination.

<<Photoacid Generator>>

Examples of the photoacid generator include onium salt photoacid generators such as bis(4-t-butylphenyl) iodonium trifluoromethane sulfonate and triphenyl sulfonium trifluoromethane sulfonate; halogen-containing compound photoacid generators such as phenyl-bis (trichloromethyl)-s-triazine; sulfonic acid photoacid generators such as benzoin tosylate and N-hydroxy succinimide trifluoromethane sulfonate; and the like. A content of the photoacid generator is preferably 0.2 to 10 parts by mass, and more preferably 0.4 to 5 parts by mass, based on 100 parts by mass of all film-forming components in the hard-mask forming composition. The photoacid generator may be used alone, or two or more types may be used in combination.

<<Absorbent>>

Examples of the absorbent include commercially available absorbents listed in "Technology and Market for Industrial Dyes" (published by CMC) and "Dyes Handbook" (edited by the Society of Synthetic Organic Chemistry), for example, C. I. Disperse Yellow 1, 3, 4, 5, 7, 8, 13, 23, 31, 49, 50, 51, 54, 60, 64, 66, 68, 79, 82, 88, 90, 93, 102, 114 and 124; C. I. Disperse Orange 1, 5, 13, 25, 29, 30, 31, 44, 57, 72 and 73; C. I. Disperse Red 1, 5, 7, 13, 17, 19, 43, 50, 54, 58, 65, 72, 73, 88, 117, 137, 143, 199 and 210; C. I. Disperse Violet 43; C. I. Disperse Blue 96; C. I. Fluorescent Brightening Agent 112, 135 and 163; C. I. Solvent Orange 2 and 45; C. I. Solvent Red 1, 3, 8, 23, 24, 25, 27 and 49; C. I. Pigment Green 10; C. I. Pigment Brown 2; and the like.

A content of the absorbent is preferably 10 parts by mass or less, and more preferably 5 parts by mass or less, based on 100 parts by mass of all film-forming components in the hard-mask forming composition. The absorbent may be used alone, or two or more types may be used in combination.

<<Rheology Modifier>>

Examples of the rheology modifier include phthalic acid derivatives such as dimethyl phthalate, diethyl phthalate, diisobutyl phthalate, dihexyl phthalate, and butyl isodecyl phthalate; adipic acid derivatives such as dinormal butyl adipate, diisobutyl adipate, diisooctyl adipate, and octyl decyl adipate; maleic acid derivatives such as dinormal butyl malate, diethyl malate, and dinonyl malate; oleic acid derivatives such as methyl oleate, butyl oleate, and tetrahydrofurfuryl oleate; and stearic acid derivatives such as normal butyl stearate and glyceryl stearate. A content of the rheology modifier is preferably less than 30 parts by mass, based on 100 parts by mass of all film-forming components in the hard-mask forming composition. The rheology modifier may be used alone, or two or more types may be used in combination.

<<Adhesion Aider>>

Examples of the adhesion aider include chlorosilanes such as m-trimethylchlorosilane, dimethyl vinyl chlorosilane, methyl diphenyl chlorosilane, and chloromethyl dimethyl chlorosilane; alkoxy silanes such as trimethyl methoxy silane, dimethyl diethoxy silane, methyl dimethoxy silane, dimethyl vinylethoxy silane, diphenyl dimethoxy silane, and phenyl triethoxy silane; silazanes such as hexamethyl disilazane, N,N'-bis(trimethylsilyl) urea, dimethyl trimethyl silylamine, and trimethyl silylimidazole; silanes such as vinyltrichlorosilane, γ-chloropropyl trimethoxy silane, γ-aminopropyl triethoxy silane, and γ-glycidoxy propyl trimethoxy silane; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; urea such as 1,1-dimethylurea and 1,3-dimethylurea; thiourea compounds; and the like. A content of the adhesion aider is preferably less than 5 parts by mass, and more preferably less than 2 parts by mass, based on 100 parts by mass of all film-forming components in the hard-mask forming composition. The adhesion aider may be used alone, or two or more types may be used in combination.

<<Solvent>>

The solvent is used to dissolve the compound (SC), the resin (P), and the optional components used if needed.

Examples of the solvent include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, and dipropylene glycol; derivatives of polyhydric alcohols of compounds having an ester bond such as ethylene glycol monoacetate, diethylene glycol monoacetate, propylene glycol monoacetate, or dipropylene glycol monoacetate, compounds having an ether bond such as monoalkyl ethers or monophenyl ether such as monomethyl ether, monoethyl ether, monopropyl ether, and monobutyl ether of the polyhydric alcohols or the compound having the ester bond, and the like [among these, propylene glycol monomethyl ether acetate (PGMEA) and propylene glycol monomethyl ether (PGME) are preferable]; cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate or the like; aromatic organic solvents such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene, and mesitylene; dimethyl sulfoxide (DMSO); and the like.

Among these, it is preferred to employ PGME, PGMEA, ethyl lactate, butyl lactate, γ-butyrolactone, cyclohexanone, mixed solvents of those, and the like from a viewpoint of further improving the leveling property.

The solvent may be used alone or be a mixed solvent of two or more types of solvents. Examples of the mixed solvent include a mixed solvent of PGME and γ-butyrolactone.

The amount of the solvent used is not particularly limited, and is appropriately set to a concentration applicable to a substrate or the like, depending on the thickness of a coating film. For example, the solvent may be blended so that the total solid concentration in the hard-mask forming composition falls preferably within a range of 2% to 30% by mass, and more preferably within a range of 5% to 20% by mass.

The hard-mask forming composition of the present embodiment stated above does not contain a crosslinking agent having a small molecular weight in the related art and contains a film-forming component having self-crosslinking properties, that is, at least one selected from the group consisting of the compound (SC) and the resin (P). For this reason, the hard-mask forming composition of the present embodiment has higher etching resistance, and also has excellent solvent resistance and heat resistance, compared to the related art.

In addition, since the hard-mask forming composition of the present embodiment does not contain a low molecular weight crosslinking agent, generation of outgassing during baking when processing the support is suppressed, and crack resistance is also excellent.

(Method for Manufacturing Electronic Component)

Specific examples of the method for manufacturing an electronic component according to second to fourth aspects of the present invention will be described with reference to FIGS. 1 to 8.

First Embodiment

The method for manufacturing an electronic component of a first embodiment includes steps of: forming a hard mask layer (m1) on a support using the hard-mask forming composition stated above (hereinafter, referred to as "Step (i-i)"); and processing the support using the hard mask layer (m1) as a mask (hereinafter, referred to as "Step (i-a)").

FIG. 1 shows a support 10 formed of a substrate 11 and a processing layer 12.

Figure 2:
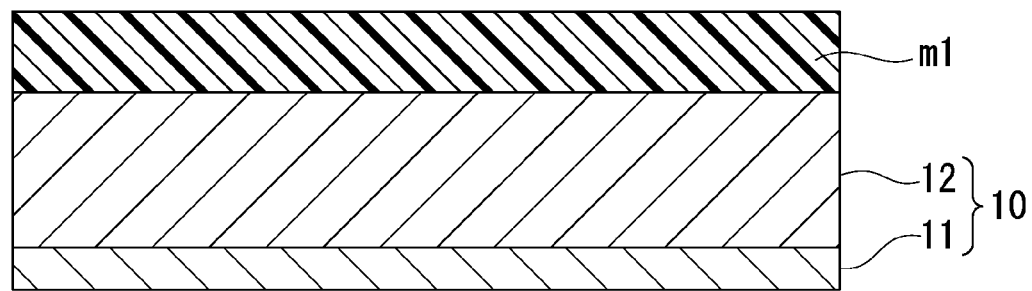
FIG. 2 is a view illustrating an exemplified process of forming a hard mask layer (m1) in the method for manufacturing an electronic component according to the embodiment of the present invention.

First, the hard mask layer (m1) is formed on the support 10 using the hard-mask forming composition according to the embodiment stated above (FIG. 2; Step (i-i)).

[Step (i-i)]

Step (i-i) is a step of forming the hard mask layer (m1) on the support 10 using the hard-mask forming composition according to the embodiment stated above.

The substrate 11 is not particularly limited and a known substrate in the related art can be used. Examples thereof include a substrate for an electronic component, a substrate on which a predetermined wiring pattern is formed, and the like. More specifically, examples of the substrate include silicon wafers, metal substrates made of copper, chromium, iron, and aluminum, glass substrates, and the like. As a material of the wiring pattern, copper, aluminum, nickel, gold, and the like can be used, for example.

Examples of the processing layer 12 include various low-k films such as films of Si, $SiO_2$, SiON, SiN, p-Si, α-Si, W, W—Si, Al, Cu and Al—Si, and stopper films thereof. The processing layer 12 usually has a thickness of 50 to 10,000 nm. In addition, in a case of performing deep processing, the thickness of the processing layer 12 may fall within a range of 1,000 to 10,000 nm.

The support 10 may not have the processing layer 12, but in a case of forming the processing layer 12, the substrate 11 and the processing layer 12 are usually made of different materials.

The hard mask layer (m1) is formed using the hard-mask forming composition according to the embodiment stated above. Specifically, the hard-mask forming composition according to the embodiment stated above is applied onto the support 10 by spin coating or the like. Subsequently, the hard mask layer (m1) is formed by baking and curing.

Baking is usually performed within a range of 100° C. to 500° C., preferably within a range of 200° C. to 450° C., and more preferably within a range of 250° C. to 400° C. The baking temperature is adjusted to be equal to or less than the upper limit value of the range, and thus it is possible to suppress decrease in etching resistance due to the oxidation reaction of the film-forming component. In addition, the baking temperature is adjusted to be equal to or higher than the lower limit value of the range, and thus it is possible to suppress deterioration due to high temperature in the steps to be stated later.

The baking time usually falls within a range of 10 to 600 seconds, preferably within a range of 30 to 300 seconds, and more preferably within a range of 50 to 200 seconds.

The film thickness of the hard mask layer (m1) is not particularly limited, and can be appropriately set according to the thickness of the processing layer 12. The film thickness of the hard mask layer (m1) may fall within a range of 30 to 20,000 nm. In addition, in a case of performing deep processing, the film thickness of the hard mask layer (m1) is preferably 500 nm or more. In this case, the film thickness of the hard mask layer (m1) falls preferably within a range of 500 to 20,000 nm, and more preferably within a range of 1,000 to 15,000 nm.

[Step (i-a)]

Step (i-a) is a step of processing the support 10 using the hard mask layer (m1) as a mask. The support 10 can be processed by, for example, performing etching using the hard mask layer (m1) as a mask. A method of etching is not particularly limited, and common dry etching and the like can be used.

In the method for manufacturing an electronic component of the first embodiment stated above, the hard mask layer (m1) is formed using the hard-mask forming composition according to the embodiment stated above, and thus it is possible to manufacture an electronic component having higher etching resistance and excellent solvent resistance and heat resistance with high quality and stability.

Second Embodiment

The method for manufacturing an electronic component of a second embodiment includes steps of: forming a hard mask layer (m1) on a support using the hard-mask forming composition of the embodiment stated above (hereinafter, referred to as "Step (ii-i)"); forming a hard mask layer (m2) made of an inorganic material on the hard mask layer (m1) (hereinafter, referred to as "Step (ii-ii)"); forming a resist film on the hard mask layer (m2) (hereinafter, referred to as "Step (ii-iii)"); forming a resist pattern on the hard mask layer (m2) by exposing the resist film to light and developing the exposed resist film (hereinafter, referred to as "Step (ii-iv)"); forming an inorganic pattern by etching the hard mask layer (m2) using the resist pattern as a mask (hereinafter, referred to as "Step (ii-v)"); forming a film-forming component pattern by etching the hard mask layer (m1) using the inorganic pattern as a mask (hereinafter, referred to as "Step (ii-vi)"); and processing the support using the film-forming component pattern as a mask (hereinafter, referred to as "Step (ii-vii)").

FIG. 1 shows a support 10 formed of a substrate 11 and a processing layer 12.

First, the hard mask layer (m1) is formed on the support 10 using the hard-mask forming composition according to the embodiment stated above (FIG. 2; Step (ii-i)).

Figure 3:
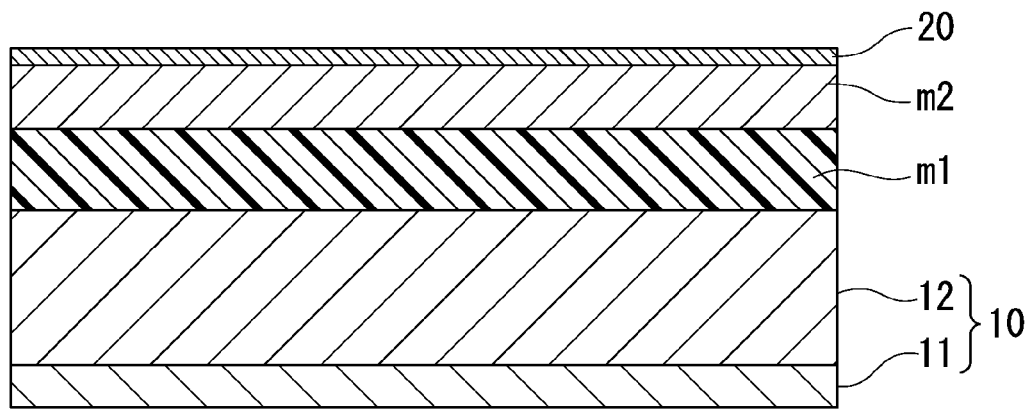
FIG. 3 is a view illustrating an exemplified process of forming a hard mask layer (m2) in the method for manufacturing an electronic component according to the embodiment of the present invention.

Subsequently, the hard mask layer (m2) made of an inorganic material is formed on the hard mask layer (m1) (FIG. 3; Step (ii-ii)). In addition, an antireflective film (BARC layer) 20 is formed on the hard mask layer (m2) if needed.

Figure 4:
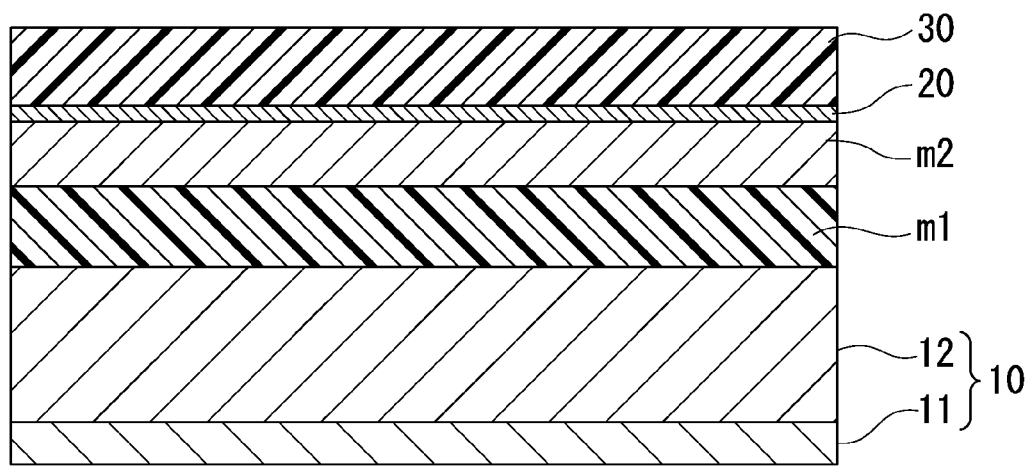
FIG. 4 is a view illustrating an exemplified process of forming a resist film in the method for manufacturing an electronic component according to the embodiment of the present invention.

Subsequently, a resist film 30 is formed on the hard mask layer (m2) using a resist composition (FIG. 4; Step (ii-iii)).

Figure 5:
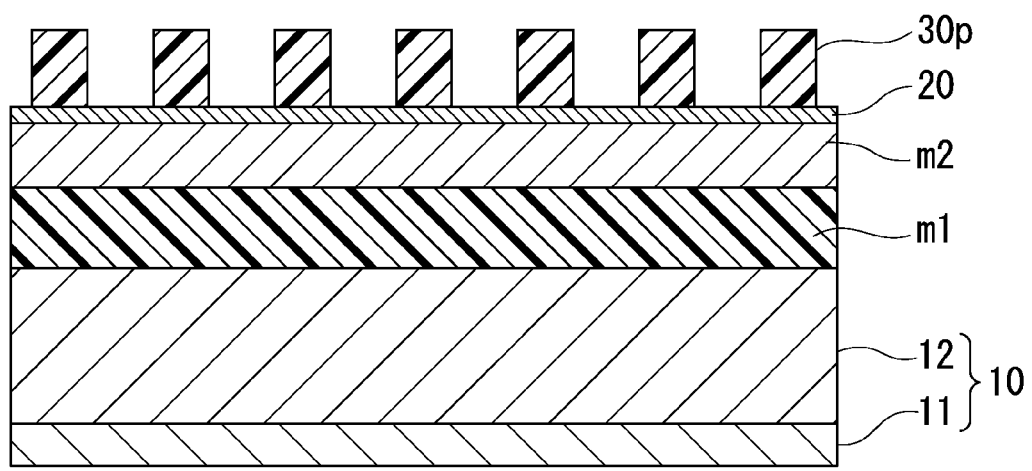
FIG. 5 is a view illustrating an exemplified process of forming a resist pattern in the method for manufacturing an electronic component according to the embodiment of the present invention.

Subsequently, a resist pattern 30p is formed on the hard mask layer (m2) by exposing the resist film to light and developing the exposed resist film (FIG. 5; Step (ii-iv)).

Figure 6:
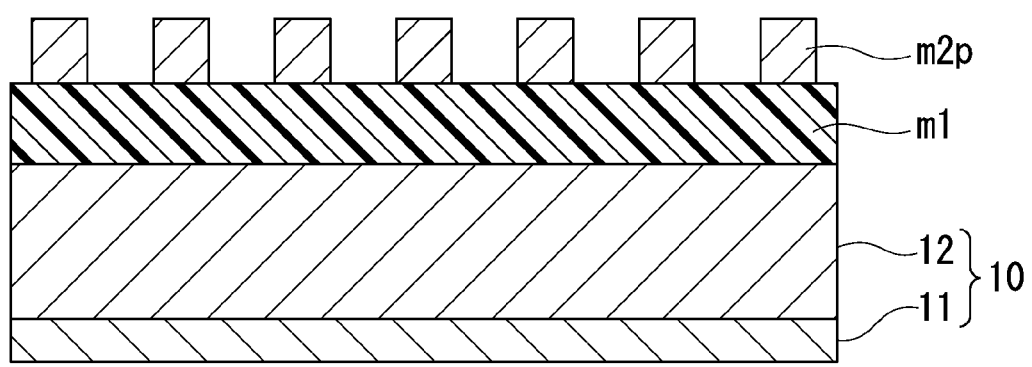
FIG. 6 is a view illustrating an exemplified process of forming an inorganic pattern in the method for manufacturing an electronic component according to the embodiment of the present invention.

Subsequently, an inorganic pattern (m2p) is formed by etching the hard mask layer (m2) using the resist pattern 30p as a mask (FIG. 6; Step (ii-v)).

Figure 7:
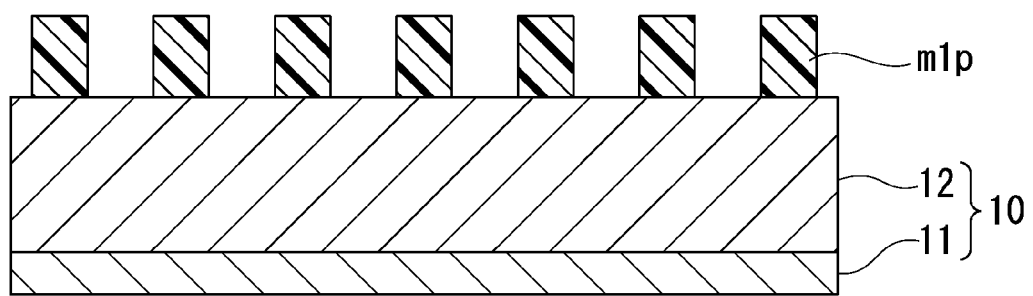
FIG. 7 is a view illustrating an exemplified process of forming a film-forming component pattern in the method for manufacturing an electronic component according to the embodiment of the present invention.

Subsequently, a film-forming component pattern (m1p) is formed by etching the hard mask layer (m1) using the inorganic pattern (m2p) as a mask (FIG. 7; Step (iii-vi)).

Figure 8:
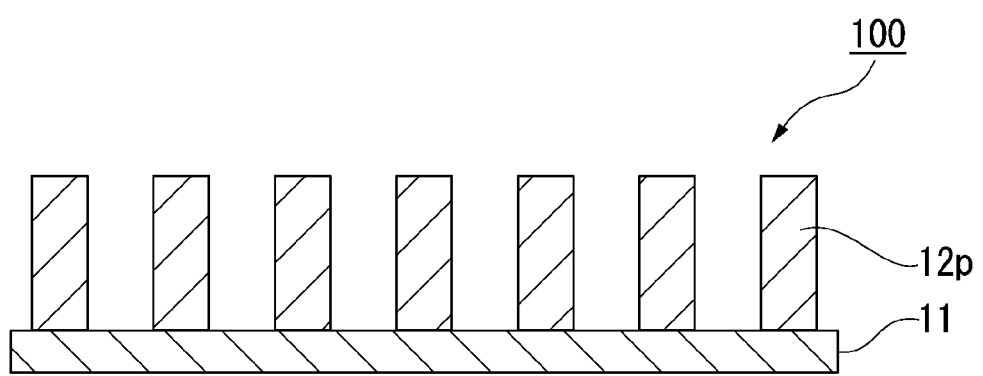
FIG. 8 is a view illustrating an exemplified process of processing a support in the method for manufacturing an electronic component according to the embodiment of the present invention.

Subsequently, a pattern 12p is formed by processing the support 10 using the film-forming component pattern (m1p) as a mask (FIG. 8; Step (ii-vii)).

Thus, the electronic component 100 provided with the pattern 12p on the substrate 11 can be manufactured.

[Step (ii-i)]

Step (ii-i) is the same as Step (i-i) stated above.

[Step (ii-ii)]

Step (ii-ii) is a step of forming the hard mask layer (m2) made of an inorganic material on the hard mask layer (m1).

The inorganic material for forming the hard mask layer (m2) is not particularly limited, and known materials in the related art can be used. Examples of the inorganic material include a silicon oxide film ($SiO_2$ film), a silicon nitride film ($Si_3N_4$ film), a silicon oxynitride film (SiON film), and the like. Among these, a SiON film having a high effect as an antireflective film is preferable. The hard mask layer (m2) can be formed by a CVD method, an ALD method, and the like.

A film thickness of the hard mask layer (m2) is, for example, about 5 to 200 nm, and preferably about 10 to 100 nm.

In a case where the CVD method or the ALD method is used to form the hard mask layer (m2), a temperature becomes high (about 400° C.), and thus the hard mask layer (m1) is required to have high temperature resistance. The hard-mask forming composition according to the embodiment stated above is excellent in heat resistance, and shrinkage is not easily generated even when exposed to a high temperature of about 400° C. For this reason, the hard-mask forming composition can be preferably used in combination with the inorganic hard mask layer formed by the CVD method or the ALD method.

After forming the hard mask layer (m2), if needed, the antireflective film (BARC layer) 20 may be formed on the hard mask layer (m2). The BARC layer 20 may be an organic BARC, or may be an inorganic BARC. The BARC layer can be formed using known methods in the related art.

[Step (ii-iii)]

Step (ii-iii) is a step of forming the resist film 30 on the hard mask layer (m2) using a resist composition.

The resist composition is not particularly limited, and those proposed as a resist material suitable for a method using an exposure step can be generally used. The resist composition may be a positive type or a negative type. Examples of the resist composition include those containing a base component of which solubility to a developer changes due to action of an acid, and an acid generator component that generates the acid upon exposure.

The formation of the resist film 30 is not particularly limited, and a method generally used for forming the resist film 30 may be used. For example, the resist composition is applied by a spinner on the hard mask layer (m2) (on the BARC layer 20 on the hard mask layer (m2) in a case where the BARC layer 20 is formed), and baked (post-apply baking (PAB)), for example, at a temperature of 80° C. to 150° C. for 40 to 120 seconds, and preferably for 60 to 90 seconds, thereby forming the resist film 30.

A film thickness of the resist film 30 is not particularly limited, but is generally about 30 to 500 nm.

[Step (ii-iv)]

Step (ii-iv) is a step of forming the resist pattern 30p on the hard mask layer (m2) by exposing the resist film 30 to light and developing the exposed resist film 30.

The resist film 30 can be exposed to light using an exposure apparatus such as an ArF exposure apparatus, a KrF exposure apparatus, an electron beam drawing apparatus, an EUV exposure apparatus, and the like. A wavelength used for exposure is not particularly limited, and exposure can be performed using ArF excimer laser, KrF excimer laser, $F_2$ excimer laser, EUV (extreme ultraviolet), VUV (vacuum ultraviolet), EB (electron beam), radiation such as X-ray and soft X-ray, and the like. The resist film 30 may be exposed by normal exposure (dry exposure) performed in an inert gas such as air and nitrogen, or by Liquid Immersion Lithography.

For example, the resist film 30 is selectively exposed by exposure through a photomask (mask pattern) on which a predetermined pattern is formed, or by drawing with direct irradiation of the electron beam not through a photomask, and the like. Thereafter, the resist film 30 is baked (post-exposure baking (PEB)), for example, at a temperature of 80° C. to 150° C. for 40 to 120 seconds, and for preferably 60 to 90 seconds.

Subsequently, the resist film 30 is developed. A developer used for the development can be appropriately selected from generally used developers, depending on a type of the resist composition and a development method. For example, in a case of employing an alkali development process, an alkali developer is used, and in a case of employing a solvent development process, a developer (organic developer) containing an organic solvent is used.

Examples of the alkali developer used for development in the alkali development process include 0.1% by mass to 10% by mass of a tetramethylammonium hydroxide (TMAH) aqueous solution.

Examples of the organic solvent contained in the organic developer used for development in the solvent development process include polar solvents such as a ketone solvent, an ester solvent, an alcohol solvent, a nitrile solvent, an amide solvent, an ether solvent, and the like; a hydrocarbon solvent; and the like.

The development process can be carried out by a known development method, and examples thereof include a method of immersing a support in a developer for a certain time (dipping method); a method of raising a developer on a surface of a support by surface tension and standing still for a certain time (paddling method); a method of spraying a developer on a surface of a support (spraying method); a method of continuously applying a developer while scanning a developer-coating nozzle at constant speed on a support rotating at the constant speed (dynamic dispensing method); and the like.

After the development process, the developed film is preferably rinsed. In a case of the alkali development process, the developed film is preferably rinsed using pure water, and in a case of the solvent development process, the developed film is preferably rinsed using a rinse solution containing an organic solvent.

Meanwhile, in a case of the solvent development process, after the development or rinsing, the developer or rinse solution adhering on the pattern may be removed with a supercritical fluid.

After the development or rinsing, drying is performed. In addition, depending on the case, baking may be performed (post baking) after the development.

Therefore, the resist pattern 30p can be formed on the hard mask layer (m2).

[Step (ii-v)]

Step (ii-v) is a step of forming an inorganic pattern (m2p) by etching the hard mask layer (m2) using the resist pattern 30p as a mask.

A method of etching the hard mask layer (m2) is not particularly limited, and for example, common dry etching can be used. Examples of the etching method include chemical etching such as down flow etching, chemical dry etching, and the like; physical etching such as sputter etching, ion beam etching, and the like; and chemical-physical etching such as RIE (reactive ion etching), and the like.

For example, in parallel plate RIE, a multilayer laminate is placed in a chamber of an RIE apparatus, and necessary etching gas is introduced. In a case where a high frequency voltage is applied to a holder of the multilayer laminate placed in parallel with an upper electrode in the chamber, the etching gas is made to plasma. Etching species including charged particles such as positive and negative ions or electrons, and neutral active species are present in the plasma. In a case where these etching species are adsorbed onto a lower resist layer, a chemical reaction occurs, reaction products get off the surface and are exhausted to the outside, and thereby etching is proceeded.

Examples of the etching gas used for etching the hard mask layer (m2) include halogen-based gas, for example. Examples of the halogen-based gas include hydrocarbon gas in which part or all of hydrogen atoms are substituted with halogen atoms such as fluorine atoms, chlorine atoms, and the like. More specifically, examples thereof include fluorinated carbon-based gas such as tetrafluoromethane ($CF_4$) gas, trifluoromethane ($CHF_3$) gas, and the like; carbon chloride-based gas such as tetrachloromethane ($CCl_4$) gas and the like; and the like.

[Step (ii-vi)]

Step (ii-vi) is a step of forming a film-forming component pattern (m1p) by etching the hard mask layer (m1) using the inorganic pattern (m2p) as a mask.

A method of etching is not particularly limited, and common dry etching method and the like can be used, in the same manner as in Step (ii-v). Examples of the etching gas used for etching the hard mask layer (m1) include oxygen gas, sulfur dioxide gas, halogen-based gas, and the like. For example, oxygen plasma etching using oxygen gas as the etching gas and the like are preferably exemplified.

[Step (ii-vii)]

Step (ii-vii) is a step of processing the support 10 using the film-forming component pattern (m1p) as a mask.

The support 10 can be processed by, for example, etching the processing layer 12 using the film-forming component pattern (m1p) as a mask.

A method of etching is not particularly limited, and common dry etching method and the like can be used, in the same manner as in Step (ii-vi). Examples of the etching gas used for etching the processing layer 12 include halogen-based gas.

In the method for manufacturing an electronic component according to the second embodiment, the hard mask layer (m1) can be thickened (1 µm or more) since the hard mask layer (m1) is formed using the hard-mask forming composition according to the embodiment stated above. For this reason, the film-forming component pattern formed from the hard mask layer (m1) can be preferably used as a mask for deep processing.

In the second embodiment stated above, the method for manufacturing an electronic component by the three-layer resist method has been stated above, but the electronic component may be manufactured by the two-layer resist method. In this case, the resist film 30, instead of the hard mask layer (m2), is formed on the hard mask layer (m1).

A resist pattern 30p is formed on the hard mask layer (m1) by exposing the resist film 30 and developing the exposed resist film 30 in the same manner as in Step (ii-iv).

Subsequently, the film-forming component pattern (m1p) is formed by etching the hard mask layer (m1) using the resist pattern 30p as a mask in the same manner as in Step (ii-vi).

Thereafter, a pattern 12p is formed by processing the support 10 using the film-forming component pattern (m1p) as a mask in the same manner as in Step (ii-vii).

Thus, the electronic component can also be manufactured by the two-layer resist method.

Therefore, the present invention also provides a method for manufacturing an electronic component, including steps of: forming a hard mask layer (m1) on a support using the hard-mask forming composition according to the first aspect stated above; forming a resist film on the hard mask layer (m1); forming a resist pattern on the hard mask layer (m1) by exposing the resist film and developing the exposed resist film; forming a film-forming component pattern by etching the hard mask layer (m1) using the resist pattern as a mask; and processing the support using the film-forming component pattern as a mask.

Third Embodiment

A method for manufacturing an electronic component according to a third embodiment includes steps of: forming a hard mask layer (m1) on a support using the hard-mask forming composition of the embodiment stated above (hereinafter, referred to as "Step (iii-i)"); forming an inorganic pattern made of an inorganic material on the hard mask layer (m1) (hereinafter, referred to as "Step (iii-v)"); forming a film-forming component pattern by etching the hard mask layer (m1) using the inorganic pattern as a mask (hereinafter, referred to as "Step (iii-vi)"); and processing the support using the film-forming component pattern as a mask (hereinafter, referred to as "Step (iii-vii)").

The method for manufacturing an electronic component according to the third embodiment is the same as the method for manufacturing an electronic component according to the second embodiment, except that the inorganic pattern made of the inorganic material is formed directly on the hard mask layer (m1) without forming the resist film.

Hereinafter, a specific example of the method for manufacturing an electronic component according to the present embodiment will be described with reference to FIGS. 1, 2, and 6 to 8. Here, the manufacturing method according to the present embodiment is not limited thereto.

First, the hard mask layer (m1) is formed on the support 10 using the hard-mask forming composition according to the embodiment stated above (FIGS. 1 and 2; Step (iii-i)). The present step is the same as Step (ii-i) stated above.

Subsequently, the inorganic pattern (m2p) made of an inorganic material is formed on the hard mask layer (m1) (FIG. 6; Step (iii-v)).

Examples of the inorganic material for forming the inorganic pattern (m2p) include those the same as the inorganic material as exemplified in Step (ii-ii), a resist composition containing the inorganic material, and the like. A method for forming the inorganic pattern (m2p) is not particularly limited, and known methods in the related art can be used. For example, the inorganic pattern (m2p) is formed on the hard mask layer (m1) by forming an inorganic resist film on the hard mask layer (m1) using a resist composition containing an inorganic material, and exposing the film to light and developing the exposed film.

Subsequently, the film-forming component pattern (m1p) is formed by etching the hard mask layer (m1) using the inorganic pattern (m2p) as a mask (FIG. 7; Step (iii-vi)). The present step is the same as Step (ii-vi).

Subsequently, a pattern 12p is formed by processing the support 10 using the film-forming component pattern (m1p) as a mask (FIG. 8; Step (iii-vii)). The present step is the same as Step (ii-vii) stated above.

Even in this manner, it is possible to manufacture an electronic component 100 provided with the pattern 12p on the substrate 11.

The method for manufacturing an electronic component of the third embodiment stated above is a simpler method in which steps can be omitted, compared to that of the second embodiment.

In the method for producing electronic components of each embodiment stated above, the hard mask layer (m1) is formed using the hard-mask forming composition according to the first aspect stated above, that is, a composition not containing a general crosslinking agent having a small molecular weight in the related art but containing a film-forming component having self-crosslinking property, and thus it is possible to manufacture an electronic component having higher etching resistance and excellent in solvent resistance and heat resistance with high quality and stability.

In addition, in the method for manufacturing an electronic component of each embodiment, since the hard-mask forming composition according to the first aspect stated above is adopted, outgassing is less likely to be generated at the time of baking when processing the support, and the composition has sufficient etching resistance even at a high aspect ratio of etching processing.

The present invention is not limited to each of the embodiments stated above, various modifications can be made within the scope shown in claims, and embodiments obtained by suitably combining technical means disclosed in different embodiments are also included in the technical scope of the present invention.

(Compound)

A compound according to a fifth aspect of the present invention is a compound represented by General Formula (sc-1) and is the same as <Compound (SC)> stated above.

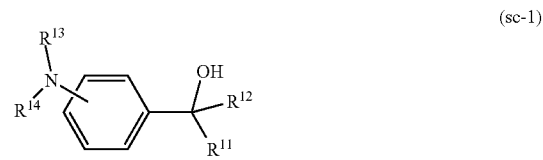

(sc-1)

[In the formula, $R^{11}$ and $R^{12}$ each independently are an organic group having 1 to 40 carbon atoms or a hydrogen atom. $R^{13}$ and $R^{14}$ each independently are an aromatic hydrocarbon group having 6 to 30 carbon atoms, which may have a substituent. Here, $R^{13}$ and $R^{14}$ may be bonded to each other to form a structure having an aromatic heterocyclic ring. In addition, a hydrogen atom of a phenylene group in the formula may be substituted with a substituent].

In Formula (sc-1), the description of $R^{11}$, $R^{12}$, $R^{13}$, and $R^{14}$ is the same as the description of $R^{11}$, $R^{12}$, $R^{13}$, and $R^{14}$ in General Formula (sc-1) described in <Compound (SC)> stated above.

A compound represented by General Formula (sc-1) of the present embodiment (compound (SC)) can be manufactured by using a known method.

Examples of the method for manufacturing the compound (SC) include a method of using reaction between a compound represented by General Formula (sc-01) (hereinafter, also referred to as "compound (SCpre)") and a metal hydride and a reaction between the compound (SCpre) and a Grignard reagent, and the like.

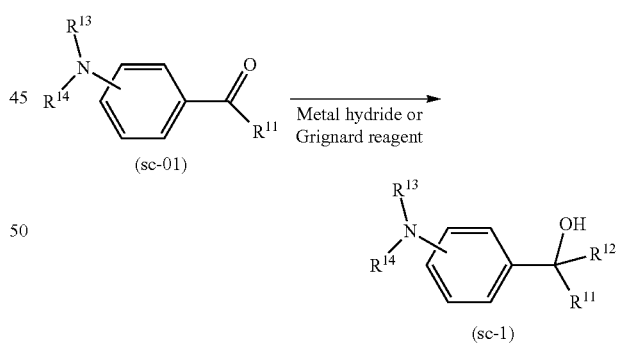

[In the formula, $R^{11}$ and $R^{12}$ each independently are an organic group having 1 to 40 carbon atoms or a hydrogen atom. $R^{13}$ and $R^{14}$ each independently are an aromatic hydrocarbon group having 6 to 30 carbon atoms, which may have a substituent. Here, $R^{13}$ and $R^{14}$ may be bonded to each other to form a structure having an aromatic heterocyclic ring. In addition, a hydrogen atom of a phenylene group in the formula may be substituted with a substituent].

The compound (SCpre) represented by General Formula (sc-01) is an intermediate (precursor) used in the process for manufacturing the compound (SC).

Details of the compound (SCpre) will be described later.

In Formula (sc-01) and Formula (sc-1), the description of $R^{11}$, $R^{12}$, $R^{13}$ and $R^{14}$ is the same as the description of $R^{11}$, $R^{12}$, $R^{13}$ and $R^{14}$ in General Formula (sc-1) described in <Compound (SC)> stated above.

As the metal hydride, for example, sodium borohydride (NaBH$_4$), lithium aluminum hydride (LiAlH$_4$), and the like can be used. In a case where a metal hydride is used, a hydrogen atom can be easily introduced into $R^{12}$ in Formula (sc-1).

As the Grignard reagent, for example, an organic magnesium halide ($R^{12}$—MgX; X represents a halogen atom) can be used. In a case where the Grignard reagent is used, an organic group having 1 to 40 carbon atoms can be easily introduced into $R^{12}$ Formula (sc-1).

The organic solvent used in the reaction between the compound (SCpre) and the metal hydride and the reaction between the compound (SCpre) and the Grignard reagent may be any solvent as long as it is a solvent in which the compounds used in each reaction are soluble and it does not react with the compounds, for example, an aprotonic polar solvent is preferable, and examples thereof include tetrahydrofuran, N,N-dimethylformamide, dimethylacetamide, dimethyl sulfoxide, sulfolane, acetonitrile, propionitrile, and the like.

[Regarding Compound (SCpre)]

The compound represented by General Formula (sc-01) (compound (SCpre)) can be manufactured by using a known method.

Examples of the method for manufacturing the compound (SCpre) include a method of reacting a compound (am-01) represented by General Formula (am-01) and a compound (ha-01) represented by General Formula (ha-01) in the presence of a base catalyst and the like.

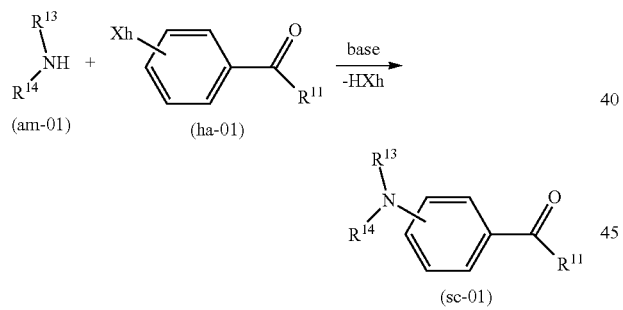

[In the formula, Xh represents a halogen atom. The description of $R^{11}$, $R^{13}$, and $R^{14}$ is the same as the description of $R^{11}$, $R^{13}$, and $R^{14}$ in General Formula (sc-1) described in <Compound (SC)> stated above.]

In Formula (ha-01), examples of Xh include a fluorine atom, a chlorine atom, a bromine atom, an iodine atom, and the like, and the fluorine atom is preferable.

Examples of the base used in the reaction between the compound (am-01) and the compound (ha-01) include organic bases such as triethylamine, 4-dimethyl aminopyridine, pyridine, ethyldiisopropyl aminocarbodiimide (EDCI) hydrochloride, dicyclohexyl carboxyimide (DCC), diisopropyl carbodiimide, carbodiimidazole, and potassium tert-butoxide; inorganic bases such as sodium hydride, K$_2$CO$_3$, and Cs$_2$CO$_3$; and the like.

The organic solvent used in the reaction between the compound (am-01) and the compound (ha-01) may be any solvent as long as it is a solvent in which the compounds used in the reaction are soluble and it does not react with the compounds, for example, an aprotic polar solvent is preferable, and examples thereof include N,N-dimethylformamide, dimethylacetamide, dimethyl sulfoxide, sulfolane, γ-butyrolactone, and the like.

Specific examples of the compound (SCpre) represented by the General Formula (sc-01) are shown below.

Compound A1

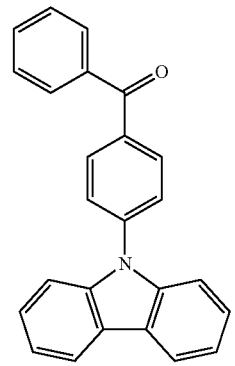

Compound A2

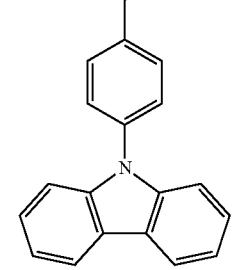

Compound A4

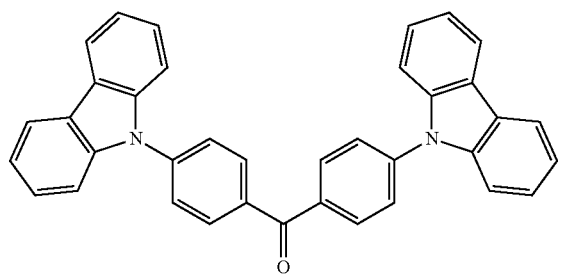

Compound A3

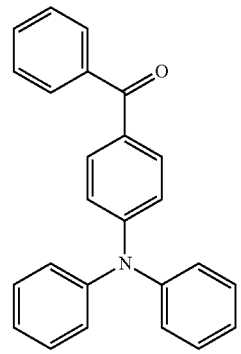

The compound (compound (SC)) of the present embodiment stated above has self-crosslinking property, and when used as a base component of a hard mask layer, the compound has higher etching resistance, and more improved solvent resistance and heat resistance. That is, such a compound (SC) is a useful material as a film-forming component in the hard-mask forming composition stated above.

(Resin)

A resin according to a sixth aspect of the present invention is a resin having a partial structure represented by General Formula (sc-p1), and is the same as <Resin (P)> stated above.

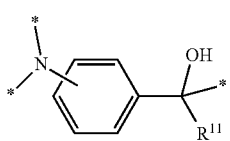

(sc-p1)

[In the formula, $R^{11}$ is an organic group having 1 to 40 carbon atoms or a hydrogen atom. The hydrogen atom of the phenylene group in the formula may be substituted with a substituent].

In Formula (sc-p1), the description of $R^{11}$ is the same as the description of $R^{11}$ in General Formula (sc-p1) described in <Resin (P)> stated above.

The resin (resin (P)) of the present embodiment can be manufactured by using a known method.

Examples of a method for manufacturing the resin (P) include a method of using a reaction between a resin having a partial structure represented by General Formula (sc-p01) (hereinafter, also referred to as "resin (Ppre)") and a metal hydride, and a reaction between the resin (Ppre) and a Grignard reagent, and the like.

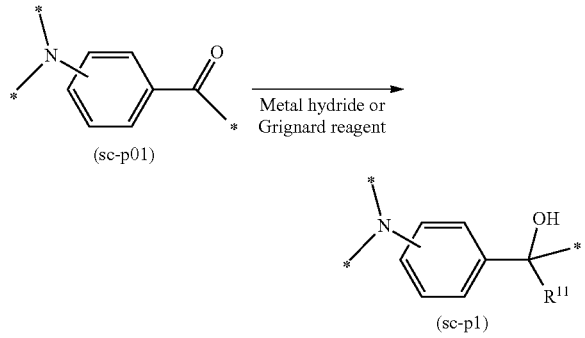

The resin (Ppre) having a partial structure represented by General Formula (sc-p01) is an intermediate (precursor) used in the process for manufacturing the resin (P). Details of the resin (Ppre) will be described later.

As the metal hydride, for example, sodium borohydride (NaBH$_4$), lithium aluminum hydride (LiAlH$_4$), and the like can be used.

As the Grignard reagent, for example, an organic magnesium halide and the like can be used.

The organic solvent used in the reaction between the resin (Ppre) and the metal hydride and the reaction between the resin (Ppre) and the Grignard reagent may be any solvent as long as it is a solvent in which the compounds used in each reaction are soluble and it does not react with the compounds, for example, an aprotic polar solvent is preferable, and examples thereof include N, N-dimethylformamide, dimethylacetamide, dimethyl sulfoxide, sulfolane, γ-butyrolactone, and the like.

The resin (resin (P)) of the present embodiment stated above has self-crosslinking property, and by being used as a base component of a hard mask layer, the resin has higher etching resistance, and further improved solvent resistance and heat resistance. That is, the resin (P) is a useful material as a film-forming component in the hard-mask forming composition stated above.

(Compound)

A compound according to a seventh aspect of the present invention is a compound represented by General Formula (sc-01-1), and is an intermediate (precursor) used in the process for manufacturing the compound (SC) stated above.

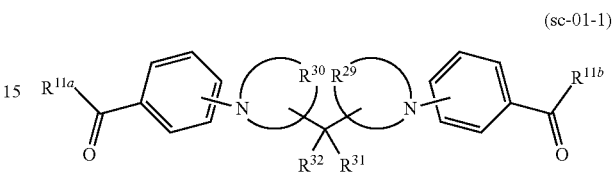

(sc-01-1)

[In the formula, $R^{11a}$ and $R^{11b}$ each independently are an organic group having 1 to 40 carbon atoms or a hydrogen atom. $R^{29}$ is a group that forms an aromatic heterocyclic ring together with a nitrogen atom. $R^{30}$ is a group that forms an aromatic heterocyclic ring together with a nitrogen atom. $R^{31}$ and $R^{32}$ each independently are an aromatic hydrocarbon group having 6 to 30 carbon atoms, which may have a substituent, or a hydrogen atom. Here, $R^{31}$ and $R^{32}$ may be bonded to each other to form a structure having an aromatic ring. In addition, the hydrogen atom of the two phenylene groups in the formula may be substituted with a substituent].

In Formula (sc-01-1), the description of $R^{11a}$ and $R^{11b}$ is the same as the description of $R^{11}$ in General Formula (sc-1-1) described in <Compound (SC)> stated above.

In Formula (sc-01-1), the description of $R^{29}$ to $R^{32}$ is the same as the description of $R^{29}$ to $R^{32}$ in General Formula (sc-1-1) described in <Compound (SC)> stated above.

The compound represented by General Formula (sc-01-1) of the present embodiment can be manufactured by using a known method.

Examples of the method for manufacturing the compound represented by General Formula (sc-01-1) include a method of reacting the compound (am-02) represented by General Formula (am-02) with the compound (ha-02) represented by General Formula (ha-02) in the presence of a base catalyst.

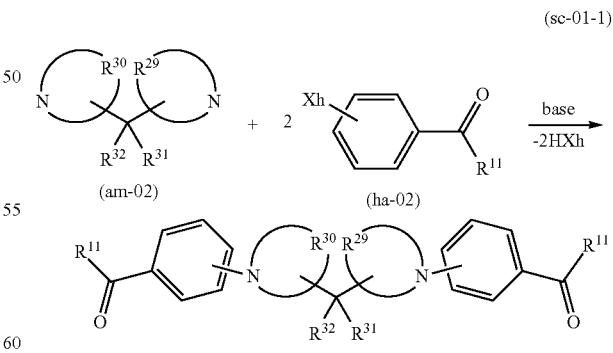

(sc-01-1)

[In the formula, Xh represents a halogen atom. The description of $R^{11}$ and $R^{29}$ to $R^{32}$ is the same as the description of and $R^{29}$ to $R^{32}$ in General Formula (sc-1-1).]

In Formula (ha-02), examples of Xh include a fluorine atom, a chlorine atom, a bromine atom, an iodine atom, and the like, and the fluorine atom is preferable.

Examples of the base used in the reaction between the compound (am-02) and the compound (ha-02) include organic bases such as triethylamine, 4-dimethyl aminopyridine, pyridine, ethyldiisopropyl aminocarbodiimide (EDCI) hydrochloride, dicyclohexyl carboxyimide (DCC), diisopropyl carbodiimide, carbodiimidazole, and potassium tert-butoxide; inorganic bases such as sodium hydride, $K_2CO_3$, and $Cs_2CO_3$; and the like.

The organic solvent used in the reaction between the compound (am-02) and the compound (ha-02) may be any solvent as long as it is a solvent in which the compounds used in the reaction are soluble and it does not react with the compounds, for example, an aprotic polar solvent is preferable, and examples thereof include N,N-dimethylformamide, dimethylacetamide, dimethyl sulfoxide, sulfolane, γ-butyrolactone, and the like.

Specific examples of the compound represented by General Formula (sc-01-1) are shown below.

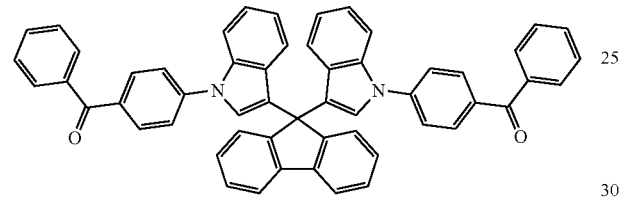

Compound A3

The compound represented by General Formula (sc-01-1) of the present embodiment stated above is an intermediate (precursor) used in the process for manufacturing the compound (SC) stated above. That is, the compound represented by General Formula (sc-01-1) is a useful raw material of the film-forming component in the hard-mask forming composition stated above.

(Resin)

A resin according to an eighth aspect of the present invention is a resin (Ppre) having a partial structure represented by General Formula (sc-p01), and is an intermediate (precursor) used in the process for manufacturing the resin (P) stated above.

(sc-p01)

The resin (resin (Ppre)) of the present embodiment can be manufactured by using a known method.

Examples of the method for manufacturing the resin (Ppre) include a method of performing a condensation reaction using the compound (SCpre), a method of performing a reaction between a diindole compound and a dihalogen compound, and the like.

Examples of the method of performing a condensation reaction using the compound (SCpre) include a method of reacting the compound (SCpre) with an aldehyde compound or a ketone compound in the presence of an acid catalyst and the like.

Examples of the aldehyde compound or the ketone compound include benzaldehyde, 1-naphthaldehyde, 1-pyrene carboxyaldehyde, 9-fluorenone, and the like.

Examples of the acid catalyst include methane sulfonic acid, hydrochloric acid, nitric acid, sulfuric acid, formic acid, oxalic acid, acetic acid, and the like.

Examples of the method of reacting the diindole compound with the dihalogen compound include a method of reacting the diindole compound with the dihalogen compound in the presence of a base catalyst and the like. Specific examples of the method for performing the reaction include a method for synthesizing a resin B6 in <Synthesis Example (7)> to be described later.

Specific examples of structural units constituting the resin (Ppre) are shown below.

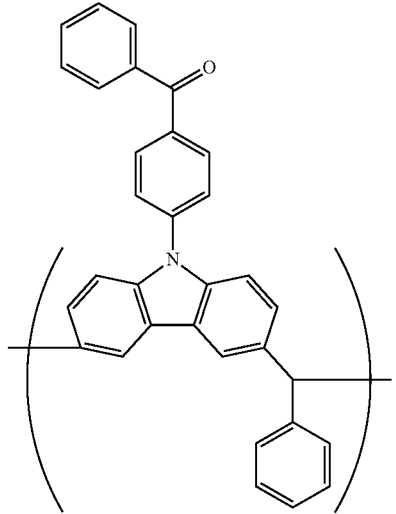

(sc-p01-1)

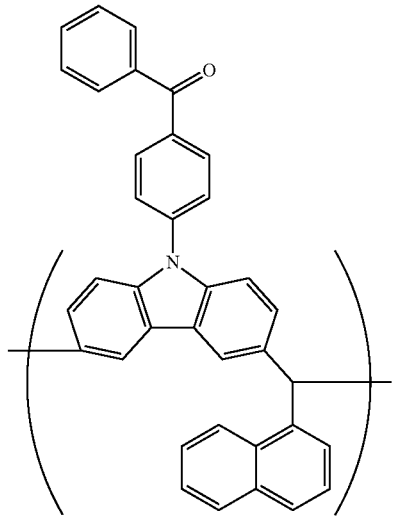

(sc-p01-2)

(sc-p01-3)

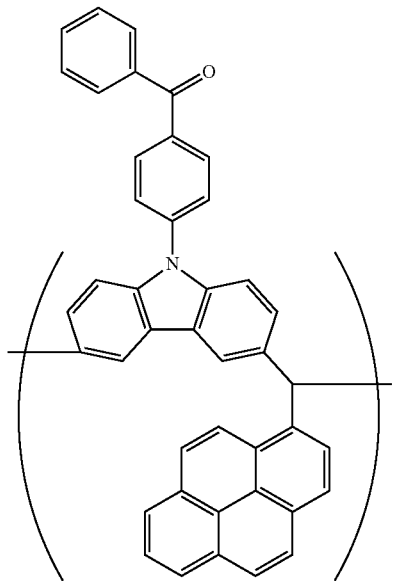

(sc-p01-4)

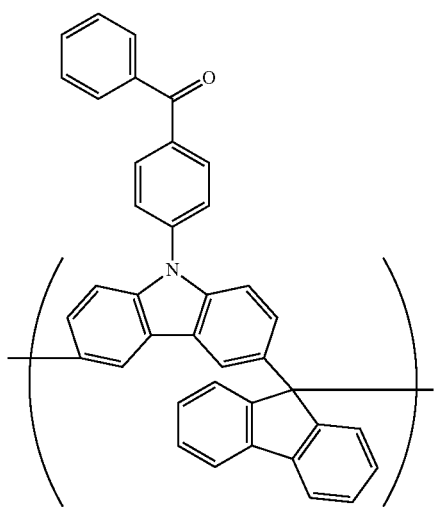

(sc-p01-5)

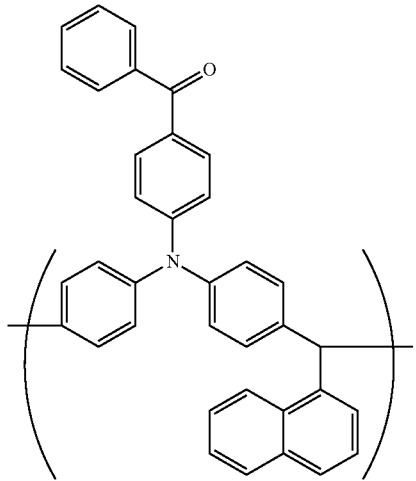

(sc-p01-6)

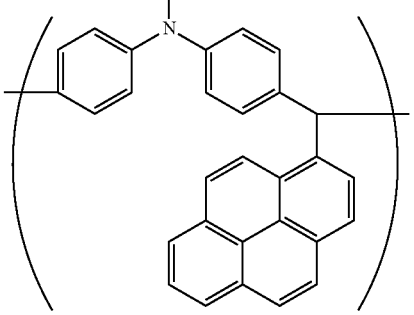

(sc-p01-7)

(sc-p01-8)

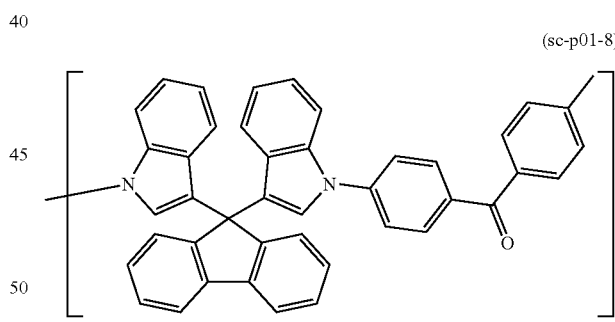

The resin (Ppre) having a partial structure represented by General Formula (sc-p01) of the present embodiment stated above is an intermediate (precursor) used in the process for manufacturing the resin (P) stated above. That is, such a resin (Ppre) is a useful raw material for a film-forming component in the hard-mask forming composition stated above.

Examples

Hereinafter, the present invention will be described in more detail referring to examples. However, the present invention is not limited to these examples.

Synthesis Example (1)

Synthesis of Compound A1:

In a three-necked flask having a capacity of 300 mL, 16.7 g of carbazole (100 mmol, manufactured by Tokyo Chemical Industry Co., Ltd.), 20 g of 4-fluorobenzophenone (100 mmol, manufactured by Tokyo Chemical Industry Co., Ltd.), 16 g of potassium carbonate (115 mmol, manufactured by Tokyo Chemical Industry Co., Ltd.) and 115 g of sulfolane (manufactured by Tokyo Chemical Industry Co., Ltd.) heated and dissolved in hot water were mixed, and the mixture was heated to 160° C. while stirring to start the reaction. After six hours therefrom, the mixture was allowed to be cooled to 60° C., and then 150 g of pure water was added thereto little by little while stirring. The precipitated product was filtered and washed 3 times with 150 g of a 1:1 mixed solution of methanol and water. The obtained yellowish white solid was vacuum dried for 24 hours to obtain 32 g of a compound A1.

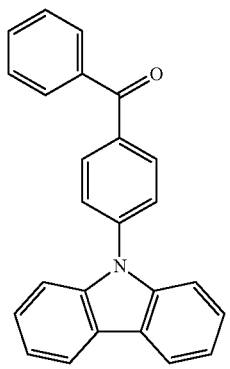

Compound A1

The obtained compound A1 was subjected to NMR measurement, and the molecular structure was identified from the following analysis results.

$^1$H-NMR (600 MHz, CDCl$_3$) δ (ppm)=6.5-8.0 (m, 17H, ArH)

$^{13}$C-NMR (150 MHz, THF) δ (ppm)=108-160 (24C, ArC), 194 (1C, C=O)

Synthesis of Resin B1:

In a three-necked flask with a capacity of 100 mL, 7.0 g (20 mmol) of compound A1, 2.3 g (22 mmol, manufactured by Kanto Chemical Co., Inc.) of benzaldehyde, and 15 g of γ-butyrolactone were mixed, 1.9 g of methane sulfonic acid (20 mmol, manufactured by Tokyo Chemical Industry Co., Ltd.) was added thereto while stirring, and the temperature was raised to 120° C. while stirring to start the reaction. After 12 hours therefrom, the mixture was allowed to be cooled to room temperature, and then reprecipitated into 100 g of a 9:1 mixed solution of methanol and a 5% aqueous ammonia solution. The obtained precipitate was filtered and washed with 100 g of a 9:1 mixed solution of methanol and a 5% aqueous ammonia solution, and further washed with 100 g of methanol. The obtained gray powder was vacuum dried for 24 hours to obtain 6.4 g of resin B1.

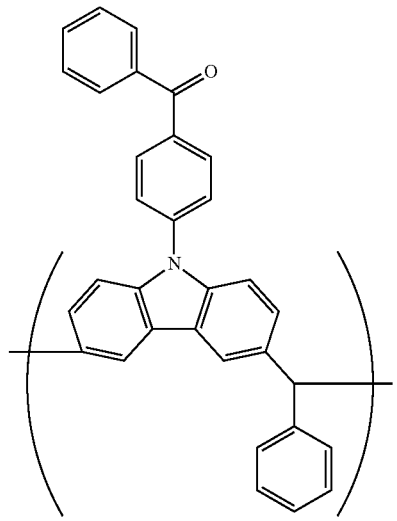

Resin B1

For the obtained resin B1, a peak at 194.5 ppm derived from the carbonyl group was observed in the $^{13}$C-NMR spectrum.

In addition, a weight average molecular weight (Mw) of the standard polystyrene conversion obtained by GPC measurement was 2,400, and a molecular weight dispersion degree (Mw/Mn) was 1.4.

Synthesis of Resin C1:

In a three-necked flask having a capacity of 200 mL, 0.87 g of sodium borohydride (23 mmol, manufactured by Tokyo Chemical Industry Co., Ltd.) and 13.6 g of dimethyl sulfoxide were mixed, heated to 50° C., stirred for 30 minutes, and dissolved. A solution prepared by mixing 5 g of resin B1 and 43 g of tetrahydrofuran was added thereto, and the mixture was refluxed in a water bath at 70° C. for 5 hours while stirring. The reaction solution was ice-cooled, and 7 mL of a 10% aqueous solution of ammonium chloride (manufactured by Tokyo Chemical Industry Co., Ltd.) was added thereto little by little while stirring. The obtained solution was poured into 700 mL of an 8:2 mixed solution of methanol and water for reprecipitation, the precipitate was filtered, washed with 100 mL of an 8:2 mixed solution of methanol and water, and further washed with 100 mL of methanol. The obtained gray powder was vacuum dried for 24 hours to obtain 4.2 g of resin C1.

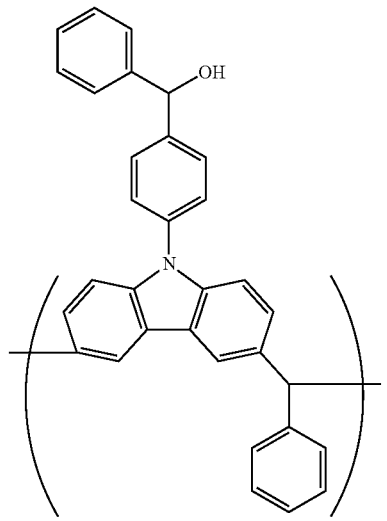

Resin C1

Regarding the obtained resin C1, in the $^{13}$C-NMR spectrum, a peak at 75.3 ppm derived from a diphenyl alcohol part was observed, and a peak derived from a carbonyl group of the resin B1 was not observed.

In addition, a weight average molecular weight (Mw) of the standard polystyrene conversion obtained by GPC measurement was 2,700, and a molecular weight dispersion degree (Mw/Mn) was 1.4.

Synthesis Example (2)

Synthesis of Resin B2 and Resin C2:

A resin B2 and a resin C2 were obtained by the same operation as in Synthesis Example (1) except that 1-naphthaldehyde (manufactured by Tokyo Chemical Industry Co., Ltd.) was used instead of benzaldehyde in <Synthesis Example (1)> stated above.

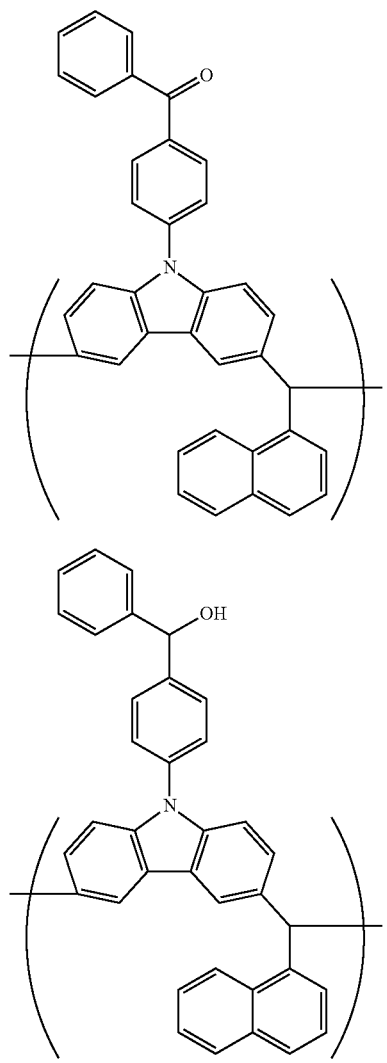

Regarding the obtained resin B2, in the $^{13}$C-NMR spectrum, a peak at 194.5 ppm derived from the carbonyl group was observed.

In addition, a weight average molecular weight (Mw) of the standard polystyrene conversion obtained by GPC measurement was 2,700, and a molecular weight dispersion degree (Mw/Mn) was 1.4.

Regarding the obtained resin C2, in the $^{13}$C-NMR spectrum, a peak at 75.3 ppm derived from the diphenyl alcohol part was observed, and a peak derived from the carbonyl group of the resin B2 was not observed.

In addition, a weight average molecular weight (Mw) of the standard polystyrene conversion obtained by GPC measurement was 2,700, and a molecular weight dispersion degree (Mw/Mn) was 1.4.

Synthesis Example (3)

Synthesis of Resin B3 and Resin C3:

A resin B3 and a resin C3 were obtained by the same operation as in Synthesis Example (1), except that 1-pyrene carboxyaldehyde (manufactured by Sigma-Aldrich) was used instead of benzaldehyde in <Synthesis Example (1)> stated above.

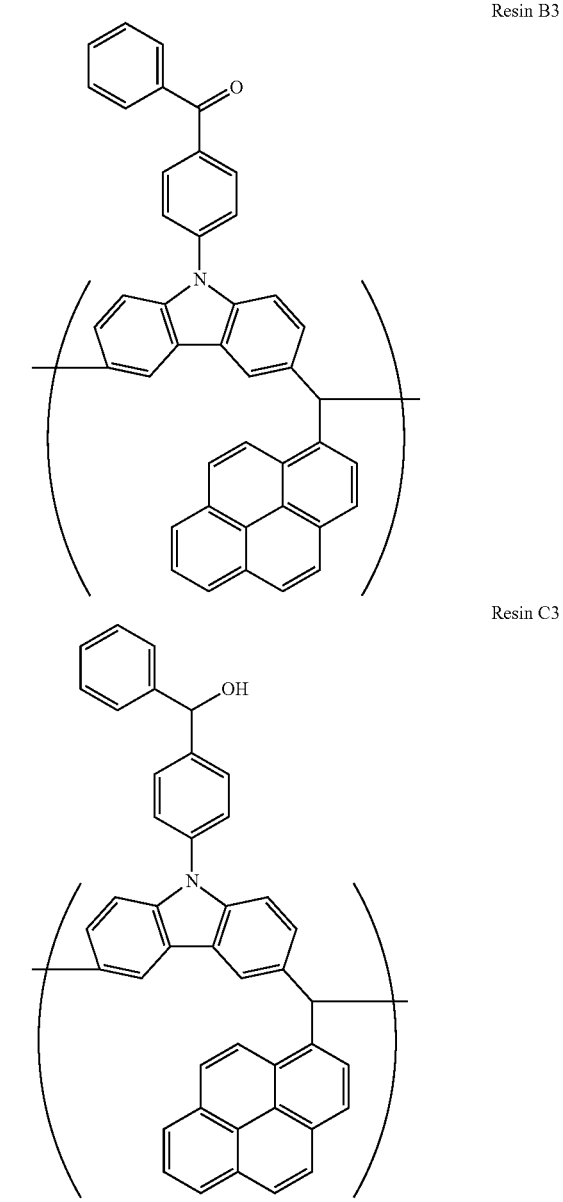

Regarding the obtained resin B3, in the $^{13}$C-NMR spectrum, a peak at 194.5 ppm derived from the carbonyl group was observed.

In addition, a weight average molecular weight (Mw) of the standard polystyrene conversion obtained by GPC measurement was 2,300, and a molecular weight dispersion degree (Mw/Mn) was 1.4.

Regarding the obtained resin C3, in the $^{13}$C-NMR spectrum, a peak at 75.3 ppm derived from the diphenyl alcohol part was observed, and a peak derived from the carbonyl group of the resin B3 was not observed.

In addition, a weight average molecular weight (Mw) of the standard polystyrene conversion obtained by GPC measurement was 2,300, and a molecular weight dispersion degree (Mw/Mn) was 1.4.

Synthesis Example (4)

Synthesis of Resin B4 and Resin C4:

A resin B4 and a resin C4 were obtained in the same operation as in Synthesis Example (1), except that 9-fluorenone (manufactured by Tokyo Chemical Industry Co., Ltd.) was used instead of benzaldehyde in <Synthesis Example (1)> stated above.

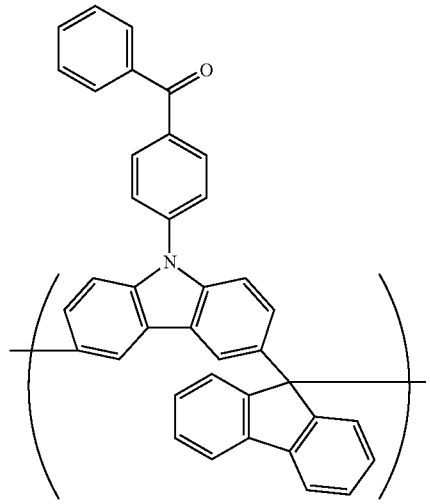

Resin B4

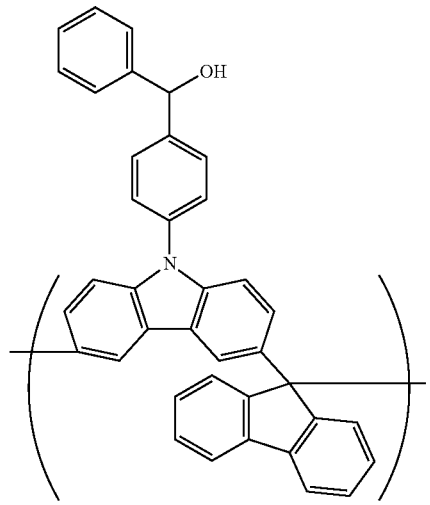

Resin C4

Regarding the obtained resin B4, in the $^{13}$C-NMR spectrum, a peak at 194.5 ppm derived from the carbonyl group was observed.

In addition, a weight average molecular weight (Mw) of the standard polystyrene conversion obtained by GPC measurement was 2,900, and a molecular weight dispersion degree (Mw/Mn) was 1.5.

Regarding the obtained resin C4, in the $^{13}$C-NMR spectrum, a peak at 75.3 ppm derived from the diphenyl alcohol part was observed, and a peak derived from the carbonyl group of the resin B4 was not observed.

In addition, a weight average molecular weight (Mw) of the standard polystyrene conversion obtained by GPC measurement was 2,900, and a molecular weight dispersion degree (Mw/Mn) was 1.5.

Synthesis Example (5)

Synthesis of Resin C5:

A resin C5 was obtained by the same operation as in Synthesis Example (1), except that a tetrahydrofuran solution of phenyl magnesium bromide (16%, manufactured by Tokyo Chemical Industry Co., Ltd.) was used instead of sodium borohydride and dimethyl sulfoxide in <Synthesis Example (1)> stated above.

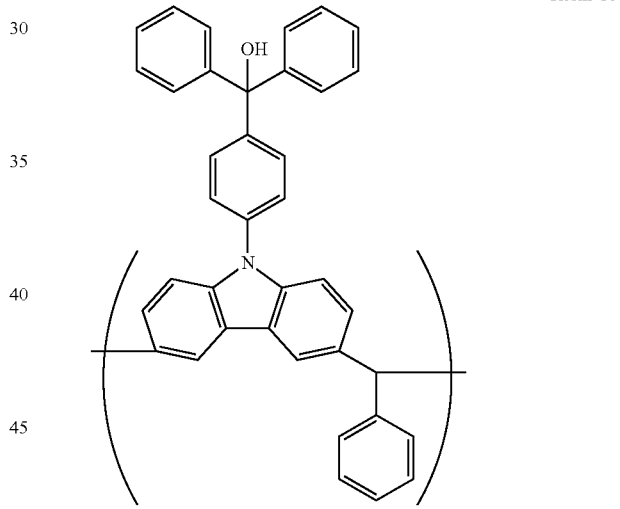

Resin C5

Regarding the obtained resin C5, in the $^{13}$C-NMR spectrum, a peak at 82.0 ppm derived from a trityl alcohol part was observed.

In addition, a weight average molecular weight (Mw) of the standard polystyrene conversion obtained by GPC measurement was 2,700, and a molecular weight dispersion degree (Mw/Mn) was 1.4.

Synthesis Example (6)

Synthesis of Compound A2:

18.4 g of carbazole (110 mmol, manufactured by Tokyo Chemical Industry Co., Ltd.), 10.9 g of 4,4-difluorobenzophenone (50 mmol, manufactured by Tokyo Chemical Industry Co., Ltd.), 16 g of potassium carbonate (115 mmol, manufactured by Tokyo Chemical Industry Co., Ltd.), and 106 g of sulfolane (manufactured by Tokyo Chemical Industry Co., Ltd.) heated and dissolved in hot water were mixed, and the mixture was heated to 160° C. while stirring to start the reaction. After eight hours therefrom, the mixture was allowed to be cooled to 60° C., and then 140 g of pure water was added thereto little by little while stirring. The precipitated product was filtered and washed 3 times with 140 g of a 1:1 mixed solution of methanol and water. The obtained yellowish white solid was vacuum dried for 24 hours to obtain 23 g of a compound A2.

Compound A2

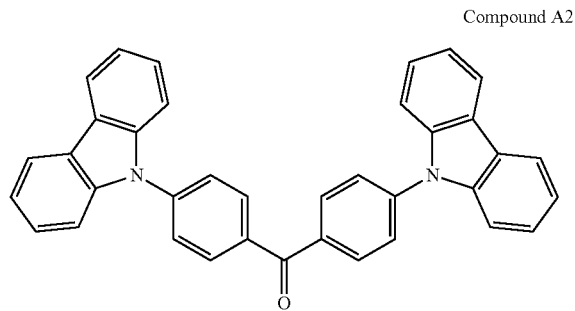 [SMILES: O=C(c1ccc(-n2c3ccccc3c3ccccc32)cc1)c1ccc(-n2c3ccccc3c3ccccc32)cc1]

The obtained compound A2 was subjected to NMR measurement, and the molecular structure was identified from the following analysis results.

$^1$H-NMR (600 MHz, CDCl$_3$) δ (ppm)=6.5-8.0 (24H, ArH)

$^{13}$C-NMR (150 MHz, THF) δ (ppm)=108-160 (36C, ArC), 194 (1C, C=O)

Synthesis of Resin B5:

5.1 g (10 mmol) of a compound A2, 3.4 g of 1-naphthaldehyde (22 mmol, manufactured by Kanto Chemical Co., Inc.), and 15 g of γ-butyrolactone were mixed, and 1.9 g (20 mmol, manufactured by Tokyo Chemical Industry Co., Ltd.) of methane sulfonic acid were added thereto while stirring, and the resultant product was heated to 120° C. while stirring to start the reaction. After 15 hours therefrom, the mixture was allowed to be cooled to room temperature and then reprecipitated into 100 g of a 9:1 mixed solution of methanol and a 5% aqueous ammonia solution. The obtained precipitate was filtered and washed with 100 g of a 9:1 mixed solution of methanol and a 5% aqueous ammonia solution, and further washed with 100 g of methanol. The obtained gray powder was vacuum dried for 24 hours to obtain 6.0 g of a resin B5.

Resin B5

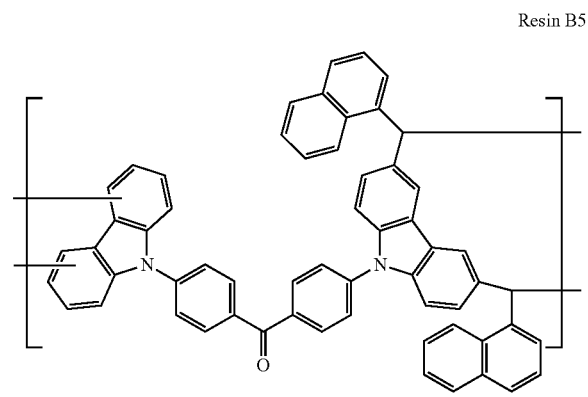

Regarding the obtained resin B5, in the $^{13}$C-NMR spectrum, a peak at 194.5 ppm derived from the carbonyl group was observed.

A weight average molecular weight (Mw) of the standard polystyrene conversion obtained by GPC measurement was 2,100, and a molecular weight dispersion degree (Mw/Mn) was 1.4.

Synthesis of Resin C6:

0.48 g (13 mmol, manufactured by Tokyo Chemical Industry Co., Ltd.) of sodium borohydride and 7.5 g of dimethyl sulfoxide were mixed, heated to 50° C., stirred for 30 minutes, and dissolved. A solution prepared by mixing 5 g of resin B5 and 40 g of tetrahydrofuran was added thereto, and the mixture was refluxed in a water bath at 70° C. for 5 hours while stirring. The reaction solution was ice-cooled, and 5 mL of a 10% aqueous solution of ammonium chloride (manufactured by Tokyo Chemical Industry Co., Ltd.) was added thereto little by little while stirring. The obtained solution was poured into 300 mL of an 8:2 mixed solution of methanol and water for reprecipitation, the precipitate was filtered, washed with 100 mL of an 8:2 mixed solution of methanol and water, and further washed with 100 mL of methanol. The obtained gray powder was vacuum dried for 24 hours to obtain 4.2 g of a resin C6.

Resin C6

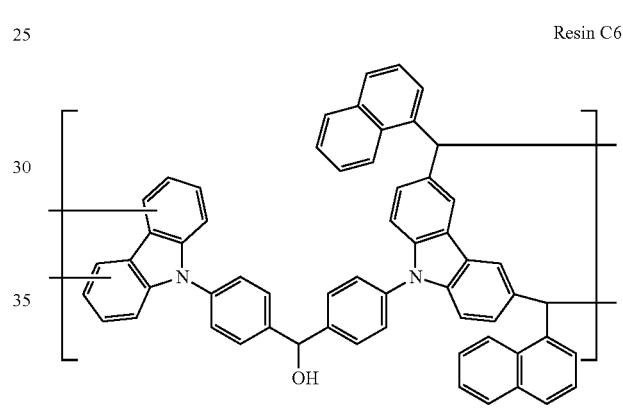

Regarding the obtained resin C6, in the $^{13}$C-NMR spectrum, a peak at 75.3 ppm derived from the diphenyl alcohol part was observed, and a peak derived from the carbonyl group of the resin B5 was not observed.

A weight average molecular weight (Mw) of the standard polystyrene conversion obtained by GPC measurement was 2,200, and a molecular weight dispersion degree (Mw/Mn) was 1.4.

Synthesis Example (7)

Synthesis of Resin B6:

In a three-necked flask having a capacity of 200 mL, 8.7 g (22 mmol) of 3,3'-(9H-fluorene-9,9-diyl) diindole, 4.4 g of 4,4-difluorobenzophenone (20 mmol, manufactured by Tokyo Chemical Industry Co., Ltd.), 5.5 g of potassium carbonate (40 mmol, manufactured by Tokyo Chemical Industry Co., Ltd.), and 20.5 g of sulfolane (manufactured by Tokyo Chemical Industry Co., Ltd.) heated and dissolved in hot water were mixed, and the mixture was raised to 160° C. while stirring to start the reaction. After 10 hours therefrom, the mixture was allowed to be cooled to 100° C., and then 39 g of γ-butyrolactone was added thereto while stirring. After allowing the solution to be cooled to room temperature, the solution was poured into 150 g of methanol for reprecipitation. After the precipitate was filtered, the resultant product was washed 3 times with 150 g of a 1:1 mixed solution of methanol and water. The obtained yellowish white solid was vacuum dried for 24 hours to obtain 11 g of a resin B6.

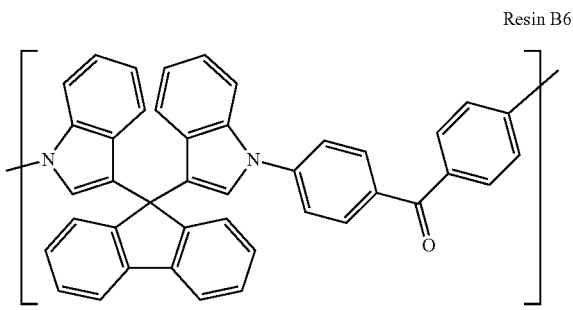

Resin B6

Regarding the obtained resin B6, in the $^{13}$C-NMR spectrum, a peak at 194.5 ppm derived from the carbonyl group was observed.

In addition, a weight average molecular weight (Mw) of the standard polystyrene conversion obtained by GPC measurement was 4,100, and a molecular weight dispersion degree (Mw/Mn) was 1.6.

Synthesis of Resin C7:

In a three-necked flask having a capacity of 200 mL, 0.92 g of sodium borohydride (24 mmol, manufactured by Tokyo Chemical Industry Co., Ltd.) and 14.5 g of dimethyl sulfoxide were mixed, and the mixture was heated to 50° C., stirred for 30 minutes, and dissolved. A solution prepared by mixing 7 g of resin B6 and 60 g of tetrahydrofuran was added thereto, and the mixture was refluxed in a water bath at 70° C. for 5 hours while stirring. The reaction solution was ice-cooled, and 7 mL of a 10% aqueous solution of ammonium chloride (manufactured by Tokyo Chemical Industry Co., Ltd.) was added thereto little by little while stirring. The obtained solution was poured into 270 g of heptane and reprecipitated, the precipitate was filtered, and then washed twice with 100 mL of a 7:3 mixed solution of methanol and water, and further washed with 100 mL of methanol. The obtained white powder was vacuum dried for 24 hours to obtain 4.2 g of a resin C7.

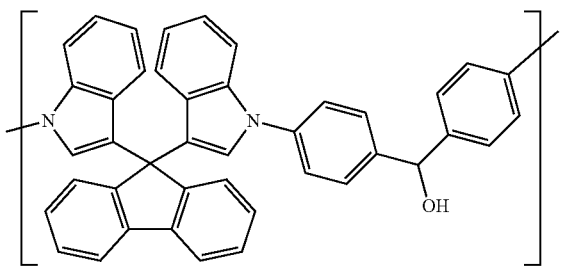

Resin C7

Regarding the obtained resin C7, in the $^{13}$C-NMR spectrum, a peak at 75.3 ppm derived from the diphenyl alcohol part was observed, and a peak derived from the carbonyl group of the resin B6 was not observed.

A weight average molecular weight (Mw) of the standard polystyrene conversion obtained by GPC measurement was 4,500, and a molecular weight dispersion degree (Mw/Mn) was 1.7.

Synthesis Example (8)

Synthesis of Compound A3:

In a three-necked flask having a capacity of 200 mL, 7.9 g (20 mmol) of 3,3'-(9H-fluorene-9,9-diyl) diindole, 10 g of 4-fluorobenzophenone (50 mmol, manufactured by Tokyo Chemical Industry Co., Ltd.), 6.9 g of potassium carbonate (50 mmol, manufactured by Tokyo Chemical Industry Co., Ltd.), and 35 g of sulfolane (manufactured by Tokyo Chemical Industry Co., Ltd.) heated and dissolved in hot water were mixed, and the mixture was heated to 160° C. while stirring to start the reaction. After 10 hours therefrom, the mixture was allowed to be cooled to 60° C. and then 115 g of pure water was added while stirring. After the precipitated precipitate was filtered, the precipitate was washed 3 times with 110 g of a 1:1 mixed solution of methanol and water, and further washed with 110 g of an 8:2 solution of methanol and acetone. The obtained yellowish white solid was vacuum dried for 24 hours to obtain 14 g of the compound A3.

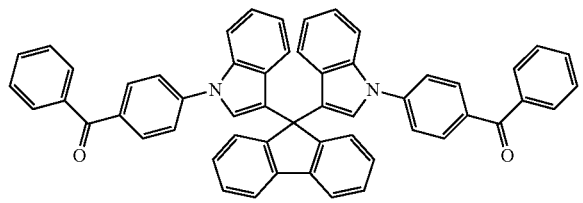

Compound A3

The obtained compound A3 was subjected to NMR measurement, and the molecular structure was identified from the following analysis results.

$^1$H-NMR (600 MHz, CDCl$_3$) δ (ppm)=6.5-8 (34H, ArH)

$^{13}$C-NMR (150 MHz, THF) δ (ppm)=57 (1C, C), 108-160 (52C, ArC), 194 (2C, C=O)

Synthesis of Compound C8:

In a three-necked flask having a capacity of 200 mL, 0.75 g of sodium borohydride (20 mmol, manufactured by Tokyo Chemical Industry Co., Ltd.) and 14 g of dimethyl sulfoxide were mixed, heated to 50° C., stirred for 30 minutes, and dissolved. A solution prepared by mixing 5 g of the compound A3 and 45 g of tetrahydrofuran was added thereto, and the mixture was refluxed in a water bath at 70° C. for 5 hours while stirring. The reaction solution was ice-cooled, and 8 mL of a 10% aqueous solution of ammonium chloride (manufactured by Tokyo Chemical Industry Co., Ltd.) was added thereto little by little while stirring. The obtained solution was poured into 240 g of an 8:2 mixed solution of methanol and pure water for reprecipitation. After the precipitate was filtered, the resultant product was washed with 100 mL of an 8:2 mixed solution of methanol and water, and further washed with 120 mL of methanol. The obtained white powder was vacuum dried for 24 hours to obtain 4.3 g of a compound C8.

Compound C8

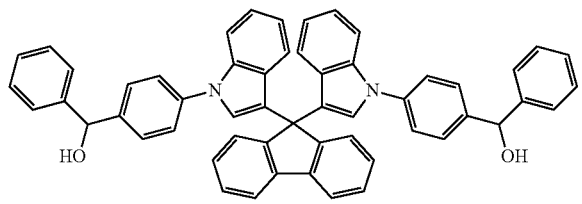

The obtained compound C8 was subjected to NMR measurement, and the molecular structure was identified from the following analysis results.

$^1$H-NMR (600 MHz, CDCl$_3$) δ (ppm)=3.2 (2H, OH), 5.7 (2H, C—OH), 6.5-8.0 (36H, ArH)
$^{13}$C-NMR (150 MHz, THF) δ (ppm)=57 (1C, C), 75 (2C, C—OH), 108-160 (52C, ArC)

Synthesis Example (9)

Synthesis of Compound C9:
A compound C9 was obtained by the same operation as in <Synthesis Example (8)>, except that a tetrahydrofuran solution of phenyl magnesium bromide (16%, manufactured by Tokyo Chemical Industry Co., Ltd.) was used instead of sodium borohydride and dimethyl sulfoxide in Synthesis Example (8)> stated above.

Compound C9

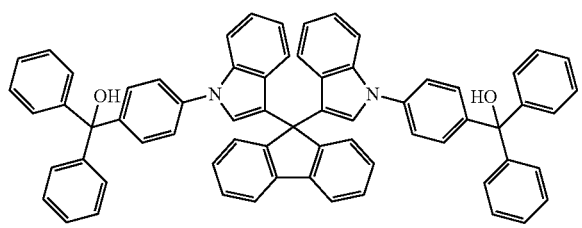

The obtained compound C9 was subjected to NMR measurement, and the molecular structure was identified from the following analysis results.
$^1$H-NMR (600 MHz, CDCl$_3$) δ (ppm)=3.2 (2H, OH), 6.5-8.0 (44H, ArH)
$^{13}$C-NMR (150 MHz, THF) δ (ppm)=57 (1C, C), 75 (2C, C—OH), 108-160 (64C, ArC)

Synthesis Example (10)

Synthesis of Compound C10:
A compound C10 was obtained by the same operation as in Synthesis Example (8) except that a tetrahydrofuran solution (10%) of Grignard reagent synthesized from 1-bromonaphthalene and magnesium by a conventional method was used instead of sodium borohydride and dimethyl sulfoxide in <Synthesis Example (8)> stated above.

Compound C10

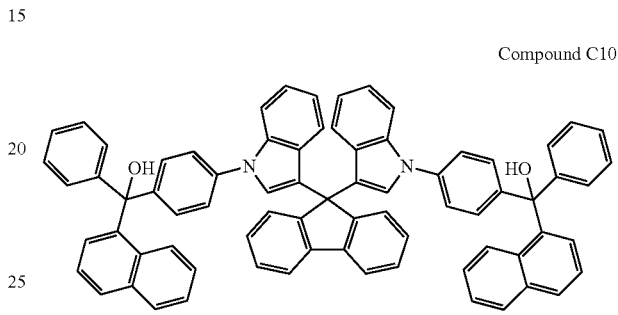

The obtained compound C10 was subjected to NMR measurement, and the molecular structure was identified from the following analysis results.
$^1$H-NMR (600 MHz, CDCl$_3$) δ (ppm)=3.2 (2H, OH), 6.5-8.0 (48H, ArH)
$^{13}$C-NMR (150 MHz, THF) δ (ppm)=57 (1C, C), 75 (2C, C—OH), 108-160 (72C, ArC)

Synthesis Example (11)

Synthesis of Compound C11:
A compound C11 was obtained by the same operation as in Synthesis Example (8) except that a tetrahydrofuran solution (10%) of a Grignard reagent synthesized from 1-bromopyrene and magnesium by a conventional method was used instead of sodium borohydride and dimethyl sulfoxide in <Synthesis Example (8)> stated above.

Compound C11

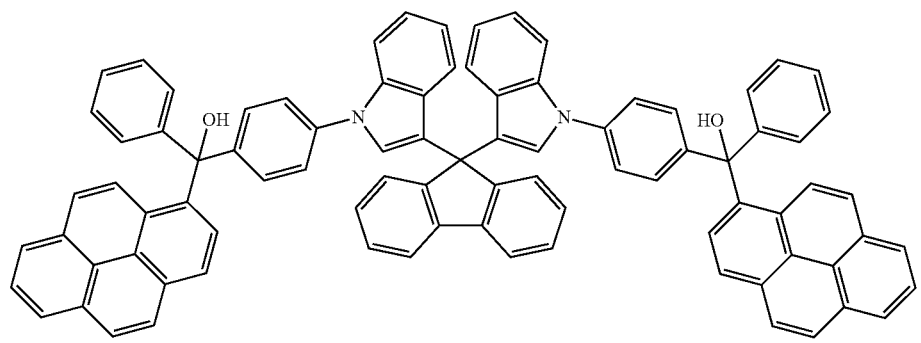

The obtained compound C11 was subjected to NMR measurement, and the molecular structure was identified from the following analysis results.

$^1$H-NMR (600 MHz, CDCl$_3$) δ (ppm)=3.2 (2H, OH), 6.5-8.0 (52H, ArH)

$^{13}$C-NMR (150 MHz, THF) δ (ppm)=57 (1C, C), 75 (2C, C—OH), 108-160 (84C, ArC)

Synthesis Example (12)

Synthesis of Compound A4:

In a three-necked flask having a capacity of 300 mL, 16.9 g of carbazole (100 mmol, manufactured by Tokyo Chemical Industry Co., Ltd.), 20 g of 4-fluorobenzophenone (100 mmol, manufactured by Tokyo Chemical Industry Co., Ltd.), 12.9 g of potassium tert-butoxide (115 mmol, manufactured by Tokyo Chemical Industry Co., Ltd.), and 115 g of sulfolane (manufactured by Tokyo Chemical Industry Co., Ltd.) heated and dissolved in hot water were mixed, and the mixture was heated to 160° C. while stirring to start the reaction. After six hours therefrom, the mixture was allowed to be cooled to 60° C., and then 150 g of a 1 M aqueous ammonium chloride solution was added thereto little by little while stirring. The precipitated product was filtered and washed 3 times with 150 g of a 1:1 mixed solution of methanol and water. The obtained yellowish white solid was vacuum dried for 24 hours to obtain 29 g of a compound A4.

Compound A4

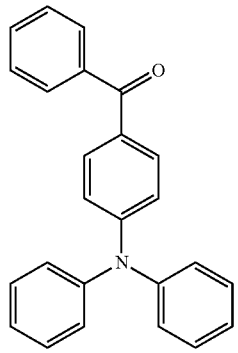

The obtained compound A4 was subjected to NMR measurement, and the molecular structure was identified from the following analysis results.

$^1$H-NMR (600 MHz, CDCl$_3$) δ (ppm)=6.5-8.0 (19H, ArH)

$^{13}$C-NMR (150 MHz, THF) δ (ppm)=108-160 (24C, ArC), 194 (1C, C=O)

Synthesis of Resin B7:

In a three-necked flask having a capacity of 100 mL, 7.0 g (20 mmol) of compound A4, 3.4 g of 1-naphthaldehyde (22 mmol, manufactured by Kanto Chemical Co., Inc.), and 18 g of γ-butyrolactone were mixed, 1.9 g of methane sulfonic acid (20 mmol, manufactured by Tokyo Chemical Industry Co., Ltd.) was added thereto while stirring, and the resultant product was heated to 100° C. while stirring to start the reaction. After 10 hours therefrom, the mixture was allowed to be cooled to room temperature and then reprecipitated into 100 g of a 9:1 mixed solution of methanol and a 5% aqueous ammonia solution. The obtained precipitate was filtered and washed with 100 g of a 9:1 mixed solution of methanol and a 5% aqueous ammonia solution, and further washed with 100 g of methanol. The obtained gray powder was vacuum dried for 24 hours to obtain 8.4 g of a resin B7.

Resin B7

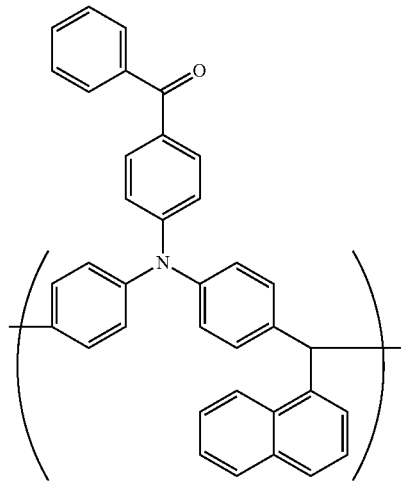

Regarding the obtained resin B7, in the $^{13}$C-NMR spectrum, a peak at 194.5 ppm derived from the carbonyl group was observed.

In addition, a weight average molecular weight (Mw) of the standard polystyrene conversion obtained by GPC measurement was 3,900, and a molecular weight dispersion degree (Mw/Mn) was 2.2.

Synthesis of Resin C12:

In a three-necked flask having a capacity of 200 mL, 0.76 g of sodium borohydride (20 mmol, manufactured by Tokyo Chemical Industry Co., Ltd.) and 12 g of dimethyl sulfoxide were mixed, heated to 50° C., stirred for 30 minutes, and dissolved. A solution prepared by mixing 5 g of resin B7 and 43 g of tetrahydrofuran was added thereto, and the mixture was refluxed in a water bath at 70° C. for 5 hours while stirring. The reaction solution was ice-cooled, and 7 mL of a 10% aqueous solution of ammonium chloride (manufactured by Tokyo Chemical Industry Co., Ltd.) was added thereto little by little while stirring. The obtained solution was poured into 700 mL of an 8:2 mixed solution of methanol and water for reprecipitation, the precipitate was filtered and then washed with 100 mL of an 8:2 mixed solution of methanol and water, and further washed with 100 mL of methanol. The obtained gray powder was vacuum dried for 24 hours to obtain 4.2 g of a resin C12.

Resin C12

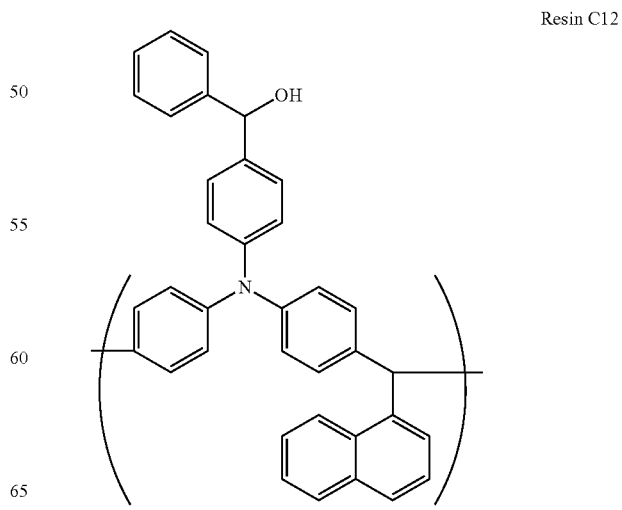

Regarding the obtained resin C12, in the $^{13}$C-NMR spectrum, a peak at 75.3 ppm derived from the diphenyl alcohol part was observed, and a peak derived from the carbonyl group of the resin B7 was not observed.

In addition, a weight average molecular weight (Mw) of the standard polystyrene conversion obtained by GPC measurement was 4,000, and a molecular weight dispersion degree (Mw/Mn) was 2.2.

Synthesis Example (13)

Synthesis of Resin B8 and Resin C13:

A resin B8 and a resin C13 were obtained by the same operation as in Synthesis Example (12) except that 1-pyrene carboxyaldehyde (manufactured by Sigma-Aldrich) was used instead of 1-naphthaldehyde in <Synthesis Example (12)> stated above.

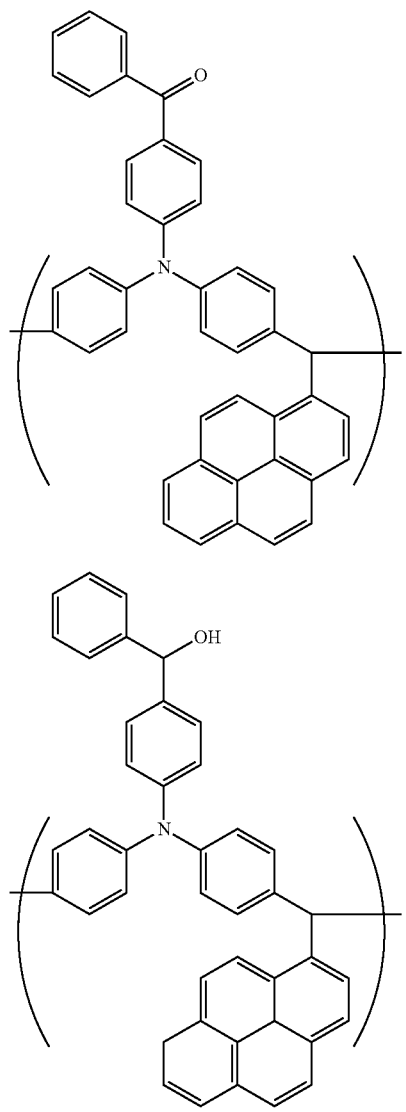

Resin B8

Resin C13

Regarding the obtained resin B8, in the $^{13}$C-NMR spectrum, a peak at 194.5 ppm derived from the carbonyl group was observed.

In addition, a weight average molecular weight (Mw) of the standard polystyrene conversion obtained by GPC measurement was 2,500, and a molecular weight dispersion degree (Mw/Mn) was 1.5.

Regarding the obtained resin C13, in the $^{13}$C-NMR spectrum, a peak at 75.3 ppm derived from the diphenyl alcohol part was observed, and a peak derived from the carbonyl group of the resin B8 was not observed.

In addition, a weight average molecular weight (Mw) of the standard polystyrene conversion obtained by GPC measurement was 2,500, and a molecular weight dispersion degree (Mw/Mn) was 1.5.

Comparative Synthesis Example (1)

Synthesis of Resin B9:

In a three-necked flask having a capacity of 500 mL, 23.5 g of 9,9'-bis(4-hydroxyphenyl) fluorene (67 mmol, manufactured by Tokyo Chemical Industry Co., Ltd.), 13.1 g of 4,4-difluorobenzophenone (60 mmol, manufactured by Tokyo Chemical Industry Co., Ltd.), 11 g of potassium carbonate (80 mmol, manufactured by Tokyo Chemical Industry), and 200 g of dimethyl sulfoxide were mixed, and the mixture was heated to 120° C. to start the reaction. After 7 hours therefrom, the solution was allowed to be cooled to room temperature, and then the solution was poured into 1,100 g of an 8:2 mixed solution of methanol and water for reprecipitation. The precipitate was filtered and washed twice with 1,100 g of an 8:2 mixed solution of methanol and water, and then further washed with 1,100 g of methanol. The obtained yellowish white powder was vacuum dried for 24 hours to obtain 32 g of a resin B9.

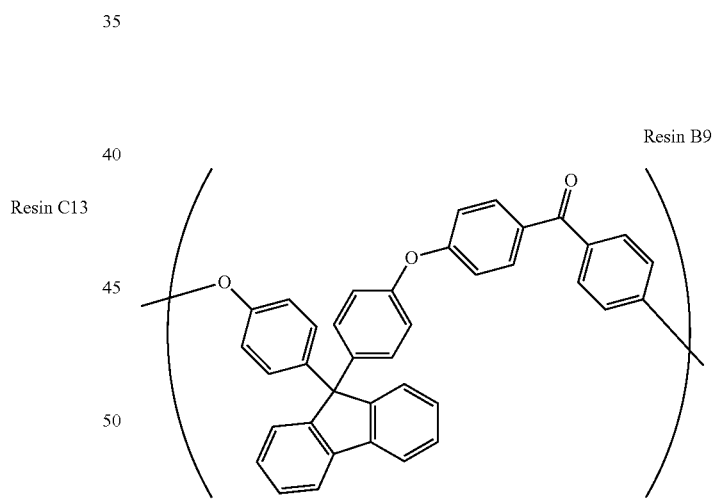

Resin B9

Regarding the obtained resin B9, in the $^{13}$C-NMR spectrum, a peak at 194.5 ppm derived from the carbonyl group was observed.

In addition, a weight average molecular weight (Mw) of the standard polystyrene conversion obtained by GPC measurement was 3,900, and a molecular weight dispersion degree (Mw/Mn) was 2.1.

Synthesis of Resin C14:

In a three-necked flask having a capacity of 200 mL, 0.9 g of sodium borohydride (24 mmol, manufactured by Tokyo Chemical Industry Co., Ltd.) and 15 g of dimethyl sulfoxide were mixed, heated to 50° C., stirred for 30 minutes, and dissolved. A solution prepared by mixing 7 g of a resin B9 and 60 g of tetrahydrofuran was added thereto, and the mixture was refluxed in a water bath at 70° C. for 5 hours while stirring. The reaction solution was ice-cooled, and 5 mL of a 5% aqueous solution of ammonium chloride (manufactured by Tokyo Chemical Industry Co., Ltd.) was added thereto little by little while stirring. The obtained solution was poured into 1,000 mL of an 8:2 mixed solution of methanol and water and reprecipitated. After the precipitate was filtered, the resultant product was washed with 500 mL of an 8:2 mixed solution of methanol and water, and further washed with 500 mL of methanol. The obtained yellowish white powder was vacuum dried for 24 hours to obtain 6.0 g of a resin C14.

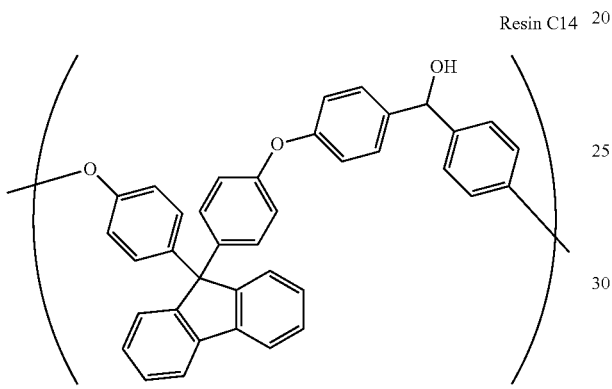

Resin C14

Regarding the obtained resin C14, in the $^{13}$C-NMR spectrum, a peak at 75.3 ppm derived from the diphenyl alcohol part was observed, and a peak derived from the carbonyl group of the resin B9 was not observed.

In addition, a weight average molecular weight (Mw) of the standard polystyrene conversion obtained by GPC measurement was 4,000, and a molecular weight dispersion degree (Mw/Mn) was 2.1.

Comparative Synthesis Example (2)

Synthesis of Resin C15:

In a three-necked flask having a capacity of 300 mL, 16.7 g of carbazole (100 mmol, manufactured by Tokyo Chemical Industry Co., Ltd.), 10.6 g of benzaldehyde (100 mmol, manufactured by Kanto Chemical Co., Inc.), 75 g of γ-butyrolactone, and 1.9 g of paratoluene sulfonic acid monohydrate (10 mmol, manufactured by Tokyo Chemical Industry Co., Ltd.) were added, and the resultant product was heated to 120° C. while stirring to start the reaction. After eight hours therefrom, the mixture was allowed to be cooled to room temperature and then reprecipitated into 450 g of an 8:2 mixed solution of methanol and a 5% aqueous ammonia solution. The obtained precipitate was filtered and washed with 480 g of an 8:2 mixed solution of methanol and a 5% aqueous ammonia solution, and further washed with 480 g of a 7:3 mixed solution of methanol and acetone. The obtained gray powder was vacuum dried for 24 hours to obtain 34 g of a resin C15.

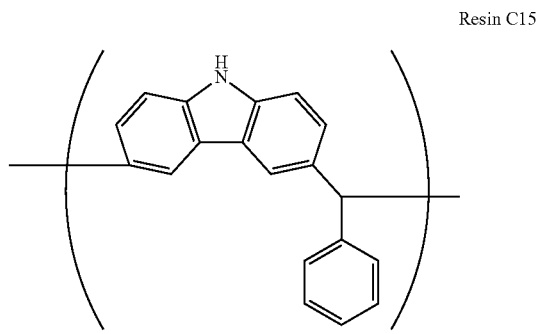

Resin C15

Regarding the obtained resin C15, a weight average molecular weight (Mw) of standard polystyrene conversion obtained by GPC measurement was 6,500, and a molecular weight dispersion degree (Mw/Mn) was 2.5.

Comparative Synthesis Example (3)

Synthesis of Resin C16:

A resin C16 was obtained by the same operation as in Comparative Synthesis Example (2), except that 1-pyrene carboxyaldehyde (manufactured by Sigma-Aldrich) was used instead of benzaldehyde in <Comparative Synthesis Example (2)> stated above.

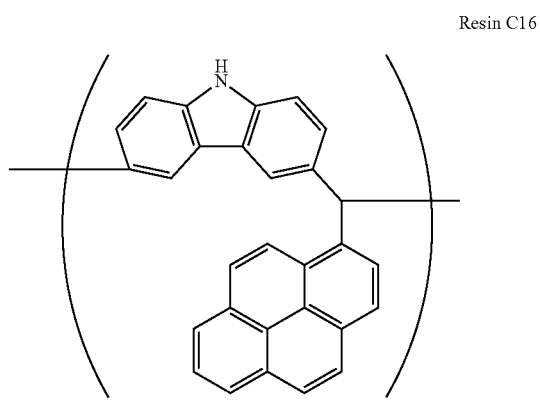

Resin C16

Regarding the obtained resin C16, a weight average molecular weight (Mw) of standard polystyrene conversion obtained by GPC measurement was 2,900, and a molecular weight dispersion degree (Mw/Mn) was 1.6.

<Preparation of Hard-Mask Forming Composition>

Each component shown in Table 1 was mixed and dissolved to prepare a hard-mask forming composition of each example (solid concentration 12.0 to 18.0% by mass).

TABLE 1

|  | Film-forming component | Thermal acid generator component | Surfactant | Solvent |
| --- | --- | --- | --- | --- |
| Example 1 | (M)-1 [100] | — | (T)-1 [2] | (A)-1 [0.1] | (S)-1 [580] |
| Example 2 | (M)-2 [100] | — | (T)-1 [2] | (A)-1 [0.1] | (S)-1 [580] |
| Example 3 | (M)-3 [100] | — | (T)-1 [2] | (A)-1 [0.1] | (S)-1 [580] |

TABLE 1-continued

| | Film-forming component | Thermal acid generator component | Surfactant | Solvent |
|---|---|---|---|---|
| Example 4 | (M)-4 [100] | — | (T)-1 [2] | (A)-1 [0.1] | (S)-1 [580] |
| Example 5 | (M)-5 [100] | — | (T)-1 [2] | (A)-1 [0.1] | (S)-1 [580] |
| Example 6 | (M)-6 [100] | — | (T)-1 [2] | (A)-1 [0.1] | (S)-1 [580] |
| Example 7 | (M)-7 [100] | — | (T)-1 [2] | (A)-1 [0.1] | (S)-1 [750] |
| Example 8 | — | (M)-8 [100] | (T)-1 [2] | (A)-1 [0.1] | (S)-1 [500] |
| Example 9 | — | (M)-9 [100] | (T)-1 [2] | (A)-1 [0.1] | (S)-1 [500] |
| Example 10 | — | (M)-10 [100] | (T)-1 [2] | (A)-1 [0.1] | (S)-1 [500] |
| Example 11 | — | (M)-11 [100] | (T)-1 [2] | (A)-1 [0.1] | (S)-1 [500] |
| Example 12 | (M)-12 [100] | — | (T)-1 [2] | (A)-1 [0.1] | (S)-1 [500] |
| Example 13 | (M)-13 [100] | — | (T)-1 [2] | (A)-1 [0.1] | (S)-1 [500] |
| Comparative Example 1 | (M)-14 [100] | — | (T)-1 [2] | (A)-1 [0.1] | (S)-1 [750] |
| Comparative Example 2 | (M)-15 [100] | — | (T)-1 [2] | (A)-1 [0.1] | (S)-1 [580] |
| Comparative Example 3 | (M)-16 [100] | — | (T)-1 [2] | (A)-1 [0.1] | (S)-1 [580] |
| Comparative Example 4 | (M)-16 [100] | (C)-1 [30] | (T)-1 [2] | (A)-1 [0.1] | (S)-1 [600] |
| Comparative Example 5 | (M)-16 [100] | (C)-2 [30] | (T)-1 [2] | (A)-1 [0.1] | (S)-1 [600] |

In Table 1, each abbreviation has the following meaning. Numerical values in [ ] are blending amounts (parts by mass).

(M)-1 to (M)-7: The above resins C1 to C7.

(M)-8 to (M)-11: The above compounds C8 to C11.

(M)-12 to (M)-13: The above resins C12 to C13.

(M)-14 to (M)-16: The above resins C14 to C16.

(C)-1: A crosslinking agent made of a compound represented by Chemical Formula (C-1).

(C)-2: A crosslinking agent made of a compound represented Chemical Formula (C-2).

(C-1)

(C-2)

(T)-1: Thermal acid generator, trade name "TAG-2689" manufactured by KING Industry.

(A)-1: Fluorinated surfactant, product name "R-40" manufactured by DIC Corporation.

(S)-1: Cyclohexanone.

<Evaluation>

Using the hard-mask forming composition of each example, etching resistance, heat resistance, and solvent resistance were evaluated by the methods shown below. These results are shown in Table 2.

[Evaluation of Etching Resistance]

The hard-mask forming composition of each example was applied onto a silicon wafer using a spin coater and baked on a hot plate at 400° C. for 60 seconds to form a hard mask layer (film thickness 500 nm).

The formed hard mask layer was subjected to dry etching, and the amount of film loss was measured to obtain an etching rate ratio.

The measurement conditions for the amount of film loss due to dry etching were set as follows.

Processing time: 3 minutes using TCP-type dry etching apparatus

Gas: $CF_4/N_2$

The etching rate ratio was calculated as a ratio of the amount of film loss of the hard mask layer to the amount of film loss of a layer made of a general cresol novolak resin represented by the following chemical formula. The lower the value is, the higher the etching resistance is.

[Evaluation of Heat Resistance]

The hard-mask forming composition of each example was applied onto a silicon wafer using a spin coater and baked on a hot plate at 240° C. for 60 seconds to form a hard mask layer (film thickness 500 nm).

For the formed hard mask layer, a 5% weight loss temperature (° C.) was measured by thermogravimetric analysis (TGA).

The TGA analysis conditions were set as follows.

Measurement temperature: 40° C. to 500° C., heating rate 10° C./min, in dry air

[Evaluation of Solvent Resistance]

The hard-mask forming composition of each example was applied onto a silicon wafer using a spin coater and baked on a hot plate at 400° C. for 60 seconds to form a hard mask layer (film thickness 500 nm).

N,N-dimethylformamide was brought into contact with the formed hard mask layer, and the solvent resistance was evaluated according to the following evaluation criteria.

Evaluation Criteria

A: In a case where the hard mask layer is not dissolved in N,N-dimethylformamide B: In a case where the hard mask layer is dissolved in N,N-dimethylformamide

TABLE 2

|  | Etching resistance Etching rate ratio | Heat resistance 5% weight reduction temperature | Solvent resistance Solvent resistance after baking |
|---|---|---|---|
| Example 1 | 0.66 | 404° C. | A |
| Example 2 | 0.62 | 470° C. | A |
| Example 3 | 0.62 | 500° C. or higher | A |
| Example 4 | 0.65 | 456° C. | A |
| Example 5 | 0.64 | 411° C. | A |
| Example 6 | 0.60 | 460° C. | A |
| Example 7 | 0.64 | 436° C. | A |
| Example 8 | 0.70 | 395° C. | A |
| Example 9 | 0.67 | 396° C. | A |
| Example 10 | 0.66 | 414° C. | A |
| Example 11 | 0.63 | 431° C. | A |
| Example 12 | 0.66 | 414° C. | A |
| Example 13 | 0.63 | 431° C. | A |
| Comparative Example 1 | 0.71 | 419° C. | A |
| Comparative Example 2 | 0.78 | 356° C. | B |
| Comparative Example 3 | 0.58 | 442° C. | B |
| Comparative Example 4 | 0.71 | 358° C. | A |
| Comparative Example 5 | 0.73 | 365° C. | A |

From the results shown in Table 2, it can be confirmed that the hard-mask forming compositions of Examples 1 to 13 have high etching resistance and are excellent in both solvent resistance and heat resistance.

On the other hand, the hard-mask forming compositions of Comparative Examples 1 to 5 were inferior in any of etching resistance, heat resistance, and solvent resistance.

Although preferable examples of the present invention have been described above, the present invention is not limited to these examples. It is possible to add, omit, replace, and change other configurations without departing from the gist of the present invention. The present invention is not limited by the above description, but only by the scope of the accompanying claims.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

10: support
11: substrate
12: processing layer
12p: pattern
20: BARC layer
30: resist film
30p: resist pattern
m1: hard mask layer
m2: hard mask layer
m1p: film-forming component pattern
m2p: inorganic pattern
100: electronic component

What is claimed is:

1. A hard-mask forming composition which forms a hard mask that is used in lithography, comprising:
a resin (P) having a structural unit (u11) represented by General Formula (u11-1),

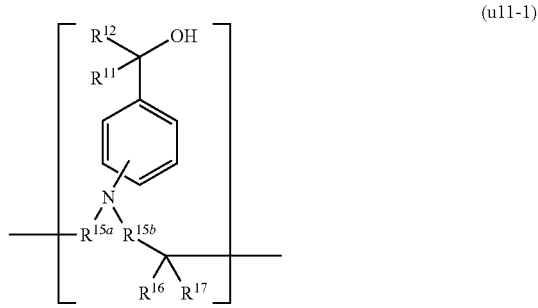

(u11-1)

wherein $R^{11}$ and $R^{12}$ are each independently an organic group having 1 to 40 carbon atoms or a hydrogen atom, $R^{15a}$ and $R^{15b}$ are each independently an aromatic hydrocarbon group having 6 to 30 carbon atoms, which may have a substituent, or a hydrogen atom $R^{15a}$ and $R^{15b}$ may be bonded to each other to form a structure having an aromatic heterocyclic ring, $R^{16}$ and $R^{17}$ are each independently an aromatic hydrocarbon group having 6 to 30 carbon atoms, which may have a substituent, or a hydrogen atom, $R^{16}$ and $R^{17}$ may be bonded to each other to form a structure having an aromatic ring, and a hydrogen atom of a phenylene group in the formula may be substituted with a substituent.

2. A method for manufacturing an electronic component, comprising:
forming a hard mask layer (m1) on a support using the hard-mask forming composition according to claim 1;
forming a hard mask layer (m2) made of an inorganic material on the hard mask layer (m1);
forming a resist film on the hard mask layer (m2);
forming a resist pattern on the hard mask layer (m2) by exposing the resist film to light and developing the exposed resist film;
forming an inorganic pattern by etching the hard mask layer (m2) using the resist pattern as a mask;
forming a film-forming component pattern by etching the hard mask layer (m1) using the inorganic pattern as a mask; and
processing the support using the film-forming component pattern as a mask.

3. A method for manufacturing an electronic component, comprising:
forming a hard mask layer (m1) on a support using the hard-mask forming composition according to claim 1;
forming an inorganic pattern made of an inorganic material on the hard mask layer (m1);
forming a film-forming component pattern by etching the hard mask layer (m1) using the inorganic pattern as a mask; and
processing the support using the film-forming component pattern as a mask.

4. A hard-mask forming composition which forms a hard mask that is used in lithography, comprising:
a resin (P) having a structural unit (u12) represented by General Formula (u12-1), (u12-1)

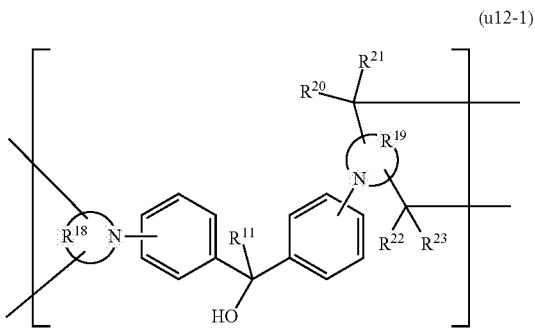

wherein $R^{11}$ is an organic group having 1 to 40 carbon atoms or a hydrogen atom, $R^{18}$ is a group that forms an aromatic heterocyclic ring together with a nitrogen atom, $R^{19}$ is a group that forms an aromatic heterocyclic ring together with a nitrogen atom, $R^{20}$ and $R^{21}$ are each independently an aromatic hydrocarbon group having 6 to 30 carbon atoms which may have a substituent, or a hydrogen atom, $R^{22}$ and $R^{23}$ may be bonded to each other to form a structure having an aromatic ring, and the hydrogen atoms of the two phenylene groups in the formula may be substituted with a substituent.

5. A hard-mask forming composition which forms a hard mask that is used in lithography, comprising:
a resin (P) having a structural unit (u13) represented by General Formula (u13-1), (u13-1)

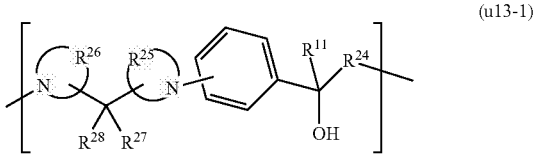

wherein $R^{11}$ is an organic group having 1 to 40 carbon atoms or a hydrogen atom, $R^{24}$ is an organic group having 1 to 40 carbon atoms, $R^{25}$ is a group that forms an aromatic heterocyclic ring together with a nitrogen atom, $R^{26}$ is a group that forms an aromatic heterocyclic ring together with a nitrogen atom, $R^{27}$ and $R^{28}$ are each independently an aromatic hydrocarbon group having 6 to 30 carbon atoms, which may have a substituent, or a hydrogen atom, $R^{27}$ and $R^{28}$ may be bonded to each other to form a structure having an aromatic ring, and a hydrogen atom of a phenylene group in the formula may be substituted with a substituent.

6. A hard-mask forming composition which forms a hard mask that is used in lithography, comprising:
a compound (SC) represented by General Formula (sc-1-1), (sc-1-1)

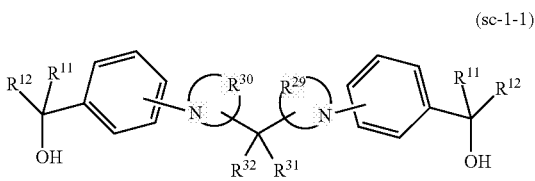

wherein $R^{11}$ is an aromatic hydrocarbon group, which may have a substituent, $R^{12}$ is an organic group having 1 to 40 carbon atoms or a hydrogen atom, $R^{29}$ is a group that forms an aromatic heterocyclic ring together with a nitrogen atom, $R^{30}$ is a group that forms an aromatic heterocyclic ring together with a nitrogen atom, $R^{31}$ and $R^{32}$ are each independently an aromatic hydrocarbon group having 6 to 30 carbon atoms, which may have a substituent, or a hydrogen atom, $R^{31}$ and $R^{32}$ may be bonded to each other to form a structure having an aromatic ring, and the hydrogen atom of the two phenylene groups in the formula may be substituted with a substituent.

7. The hard-mask forming composition according to any one of claims 1-6, further comprising a thermal acid generator component.

8. A method for manufacturing an electronic component, comprising:
forming a hard mask layer (m1) on a support using the hard-mask forming composition according to any one of claims 1-6; and
processing the support using the hard mask layer (m1) as a mask.

9. A compound represented by General Formula (sc-1-1), (sc-1-1)

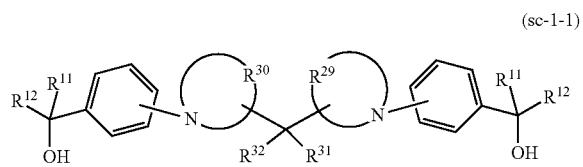

wherein $R^{11}$ is an aromatic hydrocarbon group, which may have a substituent, $R^{12}$ is an organic group having 1 to 40 carbon atoms or a hydrogen atom, $R^{29}$ is a group that forms an aromatic heterocyclic ring together with a nitrogen atom, $R^{30}$ is a group that forms an aromatic heterocyclic ring together with a nitrogen atom, $R^{31}$ and $R^{32}$ each independently are an aromatic hydrocarbon group having 6 to 30 carbon atoms, which may have a substituent, or a hydrogen atom, $R^{31}$ and $R^{32}$ may be bonded to each other to form a structure having an aromatic ring, and the hydrogen atom of the two phenylene groups in the formula may be substituted with a substituent.

10. A resin having a structural unit (u11) represented by General Formula (u11-1), (u11-1)

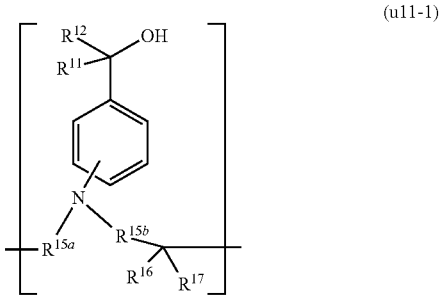

wherein $R^{11}$ bond and $R^{12}$ are each independently an organic group having 1 to 40 carbon atoms or a hydrogen atom, $R^{15a}$ and $R^{15b}$ are each independently an aromatic hydrocarbon group having 6 to 30 carbon atoms, which may have a substituent, $R^{15a}$ and $R^{15b}$ may be bonded to each other to form a structure having an aromatic heterocyclic ring, $R^{16}$ and $R^{17}$ are each independently an aromatic hydrocarbon group having 6 to 30 carbon atoms, which may have a substituent, or a hydrogen atom, $R^{16}$ and $R^{17}$ may be bonded to each other to form a structure having an aromatic ring, and a hydrogen atom of a phenylene group in the formula may be substituted with a substituent.

11. A compound represented by General Formula (sc-01-1),

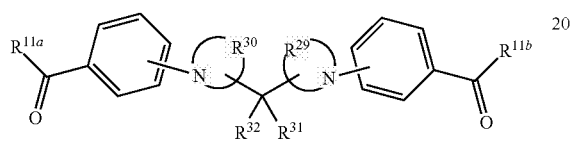
(sc-01-1)

wherein $R^{11a}$ and $R^{11b}$ are each independently a group selected from the groups represented by Formulae (org-1) to (org-8), $R^{29}$ is a group that forms an aromatic heterocyclic ring together with a nitrogen atom, $R^{30}$ is a group that forms an aromatic heterocyclic ring together with a nitrogen atom, $R^{31}$ and $R^{32}$ are each independently an aromatic hydrocarbon group having 6 to 30 carbon atoms, which may have a substituent, or a hydrogen atom, $R^{31}$ and $R^{32}$ may be bonded to each other to form a structure having an aromatic ring, and the hydrogen atom of the two phenylene groups in the formula may be substituted with a substituent

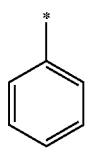
(org-1)

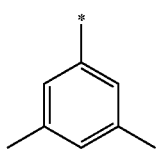
(org-2)

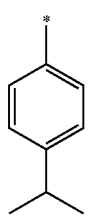
(org-3)

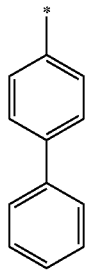
(org-4)

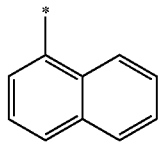
(org-5)

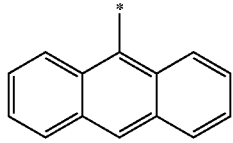
(org-6)

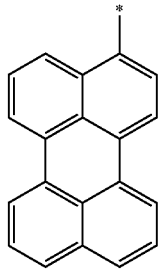
(org-7)

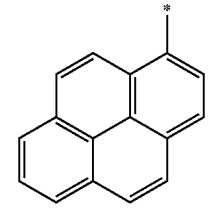
(org-8)

12. A resin having a structural unit (u12) represented by General Formula (u12-1):

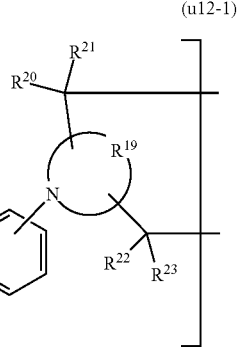
(u12-1)

wherein $R^{11}$ is an organic group having 1 to 40 carbon atoms or a hydrogen atom, $R^{18}$ is a group that forms an aromatic heterocyclic ring together with a nitrogen atom, $R^{19}$ is a group that forms an aromatic heterocyclic ring together with a nitrogen atom, $R^{20}$ and $R^{21}$ are each independently an aromatic hydrocarbon group having 6 to 30 carbon atoms, which may have a substituent, or a hydrogen atom, $R^{20}$ and $R^{21}$ may be bonded to each other to form a structure having an aromatic ring, $R^{22}$ and $R^{23}$ are each independently an aromatic hydrocarbon group having 6 to 30 carbon atoms, which may have a substituent, or a hydrogen atom $R^{22}$ and $R^{23}$ may be bonded to each other to form a structure having an aromatic ring, and the hydrogen atoms of the two phenylene groups in the formula may be substituted with a substituent.

13. A resin having a structural unit (u13) represented by General Formula (u13-1):

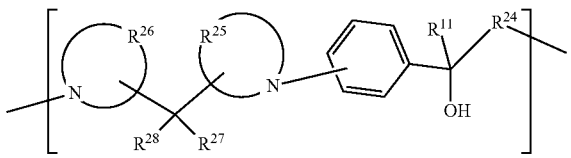

wherein $R^{11}$ is an organic group having 1 to 40 carbon atoms or a hydrogen atom, $R^{24}$ is an organic group having 1 to 40 carbon atoms, $R^{25}$ is a group that forms an aromatic heterocyclic ring together with a nitrogen atom, $R^{26}$ is a group that forms an aromatic heterocyclic ring together with a nitrogen atom, $R^{27}$ and $R^{28}$ are each independently an aromatic hydrocarbon group having 6 to 30 carbon atoms, which may have a substituent, or a hydrogen atom, $R^{27}$ and $R^{28}$ may be bonded to each other to form a structure having an aromatic ring, and a hydrogen atom of a phenylene group in the formula may be substituted with a substituent.

* * * * *